United States Patent [19]

Bloom et al.

[11] 4,139,381
[45] Feb. 13, 1979

[54] PHOTOGRAPHIC PRODUCTS AND PROCESSES EMPLOYING pH SENSITIVE FILTER DYES

[75] Inventors: Stanley M. Bloom, Waban; Alan L. Borror, Lexington; James W. Foley, Andover, all of Mass.

[73] Assignee: Polaroid Corporation, Cambridge, Mass.

[21] Appl. No.: 836,006

[22] Filed: Sep. 23, 1977

[51] Int. Cl.² .......... G03C 7/00; G03C 1/40; G03C 1/84; G03C 5/54
[52] U.S. Cl. .......... 96/3; 96/29 R; 96/63; 96/66 R; 96/73; 96/74; 96/76 R; 96/76 C; 96/77; 96/84 R; 96/112
[58] Field of Search .......... 96/3, 29 D, 74, 29 R, 96/63, 66 R, 77, 73, 76 R, 84 R, 112, 76 C

[56] References Cited

U.S. PATENT DOCUMENTS

| | | | |
|---|---|---|---|
| 3,498,789 | 3/1970 | Sutherns | 96/84 R |
| 3,647,437 | 3/1972 | Land | 96/84 R |
| 3,702,244 | 11/1972 | Bloom et al. | 96/84 R |
| 3,702,245 | 11/1972 | Simon et al. | 96/84 R |
| 3,726,675 | 4/1973 | Borror | 96/84 R |
| 3,976,659 | 8/1976 | Borror | 96/84 R |

*Primary Examiner*—Richard L. Schilling
*Attorney, Agent, or Firm*—Sybil A. Campbell

[57] ABSTRACT

This invention is concerned with photographic products, particularly diffusion transfer photographic film units, useful in photographic processes conducted outside of a camera wherein post-exposure fogging by ambient light is prevented by a compound initially present as a substantially colorless compound which is activated by base to provide a light-absorbing reagent or colored optical filter agent which is capable of being irreversibly discharged without a change in pH. The colorless compound or filter agent precursor is initially disposed in a layer of the film unit, for example, in a layer coated over the photosensitive element. Subsequent to imagewise exposure of the photosensitive element, the colored optical filter agent is generated by contacting the colorless precursor with a basic processing composition. After remaining in contact with said basic composition for a given time, the colored optical filter agent is discharged by forming a new compound which is substantially colorless and which is different from and non-reversible to said precursor and different from and non-reversible to said optical filter agent.

53 Claims, 3 Drawing Figures

PHOTOGRAPHIC PRODUCTS AND PROCESSES EMPLOYING PH SENSITIVE FILTER DYES

BACKGROUND OF THE INVENTION

1. Field of the Invention

This invention relates to photography, and more particularly, it relates to photographic processes performed in ambient light and to photographic products useful in such processes wherein the compounds employed as optical filter agents for protecting the imagewise exposed photosensitive material from further exposure during processing decolorize independently of changes in pH.

2. Description of the Prior Art

A number of diffusion transfer processes for producing photographic images in both black-and-white and in color have been proposed. Of particular interest are diffusion transfer processes wherein the image-receiving layer carrying the transfer image is not separated from the developed photosensitive layer(s) after processing but both components are retained together as a permanent laminate. Included as part of the laminate is a layer of light-reflecting material, preferably titanium dioxide, positioned between the image-carrying layer and the developed photosensitive layer(s). The light-reflecting layer separating the image-carrying and photosensitive components provides a white background for the transfer image and masks the developed photosensitive layer(s). In addition to these layers, the laminate usually includes dimensionally stable outer layers or supports, at least one of which is transparent so that the resulting transfer image may be viewed by reflection against the background provided by the light-reflecting layer. Diffusion transfer processes for forming images viewable without separation of the photosensitive and image-receiving components and integral negative-positive film units useful in such processes, i.e., film units wherein the negative or the photosensitive component and the positive or image-receiving component are retained as a permanent laminate after processing are described in U.S. Pat. Nos. 3,415,644, 3,415,645, and 3,415,646 issued Dec. 10, 1968 to Edwin H. Land, U.S. Pat. Nos. 3,573,043 and 3,573,044 issued Mar. 30, 1971 to Edwin H. Land and U.S. Pat. Nos. 3,594,164 and 3,594,165 issued July 20, 1971 to Howard G. Rogers.

U.S. Pat. No. 3,647,437 issued Mar. 7, 1972 to Edwin H. Land also is concerned with diffusion transfer processes wherein the resulting photograph comprises the developed photosensitive layer(s) retained with the image-receiving layer as part of a permanent laminate. In the processes disclosed in this patent, a photographic film unit comprising a photosensitive element is developed in ambient light but further undesired exposure during processing is prevented by a light-absorbing material or optical filter agent which is retained in the processed film unit. In a preferred embodiment, the optical filter agent is a pH-sensitive dye, i.e., a dye possessing sepctral absorption characteristics that are reversibly alterable in response to changes in environmental pH and particularly, a pH-sensitive dye having a colored or light-absorbing form above a given alkaline pH and a colorless or non-light-absorbing form below said pH. Though the pH-sensitive dye is usually included in the processing composition, it may be initially positioned in the film unit, for example, in a layer over the photosensitive element provided it is in its colorless form if photoexposure is to be effected through that layer. Upon application of an alkaline processing composition, the pH-sensitive dye is converted to its colored form, and after the desired processing time, it is converted back to its colorless form by reducing the environmental pH, e.g., by including an acid-reacting layer as part of the film unit. Examples of pH-sensitive dyes found particularly useful as optical filter agents are the phthalein and naphthalein dyes disclosed in U.S. Pat. No. 3,702,244 issued Nov. 7, 1972 to Stanley M. Bloom, Alan L. Borror, Paul S. Huyffer and Paul T. MacGregor and in U.S. Pat. No. 3,702,245 issued Nov. 7, 1972 to Myron S. Simon and David P. Waller and also the 9-pyridyl fluorene dyes disclosed in U.S. Pat. No. 3,726,675 issued Apr. 10, 1973 to Alan L. Borror.

The present invention is directed to a different class of optical filter agents and filter agent precursors useful in the above-described processes and products wherein a colored optical filter agent formed by contacting the precursor with a basic processing composition is decolorized without reversal to the precursor and without reducing the pH. Because of their ability to clear independently of a pH reduction, the subject filter agents may be employed in photographic processes where the pH of the system remains substantially unchanged subsequent to processing and also may be employed to permit early viewing of the final image in processes where the pH is reduced during the final stages of processing. Also, because the optical filter agent is irreversibly decolorized to a colorless product inert to changes in pH, the possibility of color reappearing in time due to accidentally increasing the pH is avoided.

SUMMARY OF THE INVENTION

It is, therefore, the primary object of the present invention to provide photographic processes and products which employ as optical filter agent precursors, a class of compounds activated by base to form a light-absorbing or colored optical filter agent that becomes decolorized after a predetermined time in contact with said base.

It is another object of the present invention to provide photographic products, particularly integral negative-positive diffusion transfer film units, adapted for processing in ambient light which contain (a) a substantially colorless optical filter agent precursor activated by a basic processing composition to form (b) a colored optical filter agent which, after a predetermined time in contact with said basic composition, forms (c) a substantially colorless compound which is different from said (a) and (b) and which is non-reversible to said (a) or (b) under acid, neutral or alkaline conditions.

Other objects of this invention will in part be obvious and will in part appear hereinafter.

The invention accordingly comprises the processes involving the several steps and the relation and order of one or more of such steps with respect to each of the others, and the products and compositions possessing the features, properties and the relation of elements which are exemplified in the following detailed disclosure, and the scope of the application of which will be indicated in the claims.

For a fuller understanding of the nature and objects of the invention, reference should be had to the following detailed description of the invention taken in conjunction with the accompanying drawings.

DETAILED DESCRIPTION OF THE INVENTION

Figure 1:
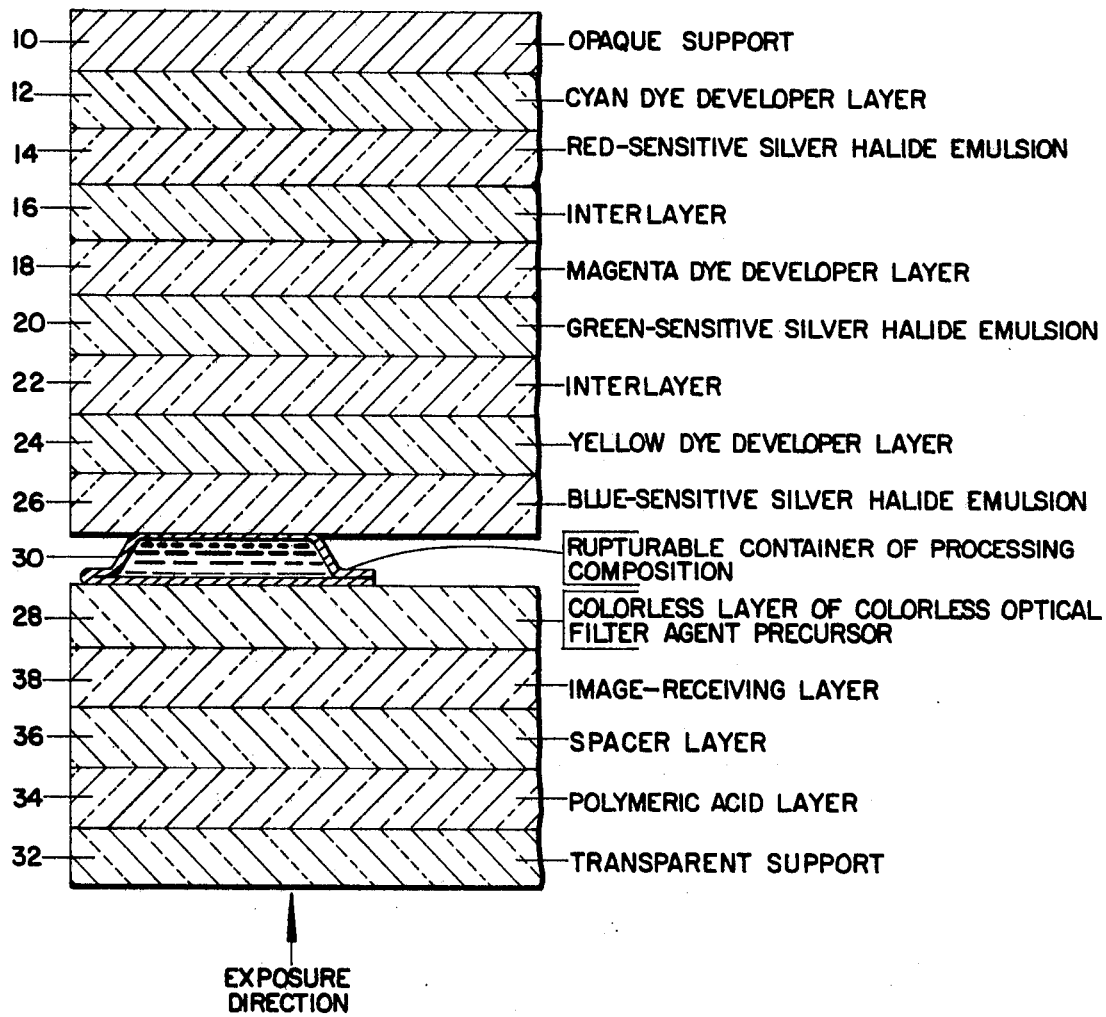
FIG. 1 is a diagrammatic enlarged cross-sectional view of a diffusion transfer film unit illustrating one embodiment of the present invention.

The present invention provides a system in which a colorless precursor of a colored compound is converted to said colored compound, and said colored compound is converted to a second, different colorless compound. These conversions are effected at an alkaline pH, the alkaline pH required for the conversion of the colored compound to the second colorless compound being at least as high as the pH required to effect conversion of the colorless precursor to the colored compound. The following description of the invention will be in terms of its preferred embodiment — the provision of temporary protection against ambient light for a developing photosensitive element.

In the preferred embodiment, a photosensitive material is protected from further exposure during processing in incident actinic light by employing (a) a substantially colorless compound, i.e., a compound which does not absorb visible radiation intended to expose the photosensitive material but which, upon contact with an aqueous solution of base having an alkaline pH above a given value forms (b) a colored compound capable of absorbing such radiation thereby preventing further exposure of said photosensitive material by ambient light, said colored compound after remaining in contact with said solution above said pH for a predetermined time forming (c) a colorless compound different from (a) and (b) and non-reversible to either (a) or (b) by a change in pH.

Compounds capable of undergoing the above-described transformations in base, wherein colorless compound (a) generates colored compound (b) and colored compound (b) in turn generates colorless compound (c) above a given alkaline pH are those possessing (i) an ionizable proton removed in base to generate a chromophore and (ii) a moiety that undergoes an irreversible cleavage reaction with said base to destroy said chromophore and yield a substantially colorless product.

Illustrative of such compounds useful as optical filter agent precursors to provide optical filter agents in accordance with the present invention are those represented by the following formula

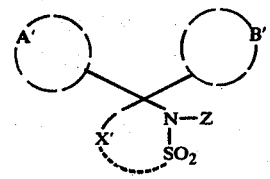

(I)

wherein A' is a 4'-hydroxyphenyl moiety or a 4'-hydroxynaphthyl moiety; B' is a phenyl moiety or a naphthyl moiety provided A' is a 4'-hydroxyphenyl moiety when B' is a naphthyl moiety; X' represents the atoms necessary to complete a ring-closing moiety selected from a 2,3-dihydrobenz[d]isothiazole-1,1-dioxide moiety and a 2,3-dihydronaphtho[1,8-de]-1,2-thiazine-1,1-dioxide moiety and Z is a moiety that undergoes irreversible cleavage in alkaline solution above a predetermined alkaline pH within a predetermined time.

The reaction sequence which these compounds undergo in base above a given alkaline pH, usually about pH 10, is illustrated below wherein the A moiety is a 4'-hydroxyphenyl moiety. It will be appreciated that the reaction sequence in base will be the same for a 4'-hydroxynaphthyl moiety, namely removal of the ionizable proton from the functional —OH which is attended by the opening of the ring-closing group to give the colored optical filter agent followed by irreversible cleavage of the Z moiety to give a new colorless compound having a different moiety, Z', on the N atom of the ring-closing group.

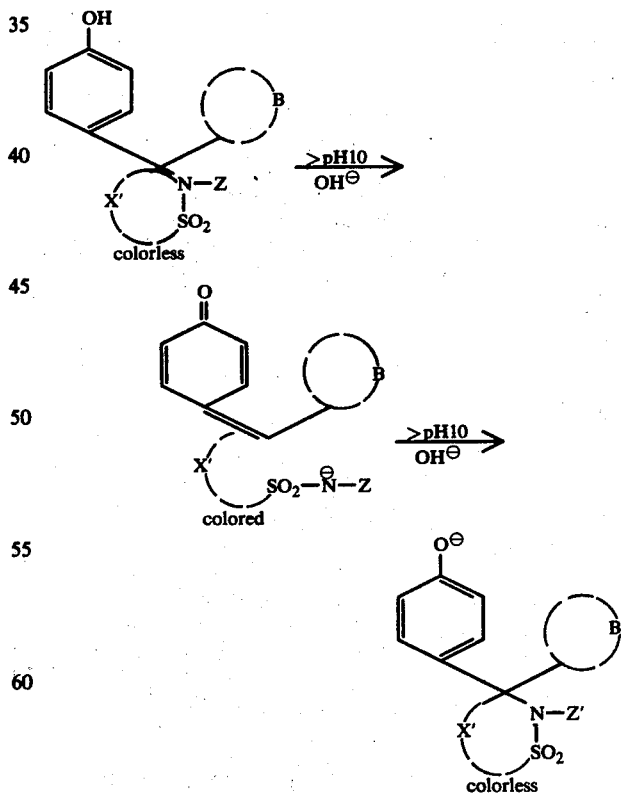

Where the irreversible cleavage of the Z moiety yields a fragment in addition to the new colorless compound, the fragment also is colorless.

It will be understood that the A' moiety and/or the B' moiety and/or the ring-closing moiety of the compounds represented in formula I above may contain one or more substituents in addition to those specified, which substituents should not interfere with the intended use of the compounds. Preferably, the moiety, Z, is a carbonyl moiety possessing a

group bonded to the N atom of the ring-closing moiety and undergoes said irreversible cleavage, for example, by alkaline hydrolysis, $E_1$ elimination or intramolecular cyclization followed by alkaline hydrolysis. In a preferred embodiment, the filter agent precursors may be represented by the formula

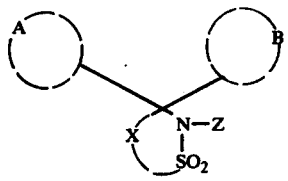

(II)

wherein A is a 4'-hydroxy-1'-phenyl moiety or a 4'-hydroxy-1'-naphthyl moiety; B is a phenyl moiety or a naphthyl moiety, provided A is said 4'-hydroxy-1'-phenyl moiety when B is said naphthyl moiety; X represents the carbon atoms necessary to complete a ring-closing moiety selected from a 2,3-dihydrobenz[d]isothiazole-1,1-dioxide moiety and a 2,3-dihydronaphtho[1,8-de]-1,2-thiazine-1,1-dioxide moiety; and Z is a carbonyl moiety containing a

group bonded to the N atom of said ring-closing moiety that undergoes an irreversible cleavage reaction in alkaline solution above a predetermined alkaline pH. Examples of mechanisms by which cleavage may occur are alkaline hydrolysis, $E_1$ elimination or intramolecular cyclization followed by alkaline hydrolysis.

Typical substituents include branched or straight chain alkyl, such as, methyl, ethyl, isopropyl, n-butyl, t-butyl, hexyl, octyl, dodecyl, hexadecyl, octadecyl and eicosanyl; aryl, such as phenyl and naphthyl; alkaryl and aralkyl, preferably, alkyl-substituted phenyl and phenyl-substituted alkyl, such as p-ethylphenyl, p-octylphenyl, p-dodecylphenyl, benzyl, phenethyl, phenylhexyl and phenyldodecyl; alkoxy, such as, methoxy, ethoxy, butoxy, octadecyloxy, 1-ethoxy-2-(β-ethoxyethoxy); aryloxy, such as, phenoxy, benzyloxy and naphthoxy; alkoxyalkyl, such as, methoxymethyl, ethoxymethyl, and dodecyloxyethyl; halo, such as, fluoro, bromo and chloro; trihalomethyl, such as, trifluoromethyl and trichloromethyl; sulfonamido (—NH—$SO_2R^0$ wherein $R^0$ is alkyl, aryl, alkaryl or aralkyl); sulfamoyl (—$SO_2$—NH—$R^0$ wherein $R^0$ has the same meaning given above); acyl (

wherein $R^0$ has the meaning given above); sulfonyl (—$SO_2$—$R^0$ wherein $R^0$ has the same meaning given above); sulfo; cyano; carboxy; hydroxy; and amino including mono- and disubstituted amino (—NR'R" wherein R' and R" each are hydrogen, alkyl, aryl, alkaryl or aralkyl and R' and R" taken together represent the atoms necessary to complete a saturated heterocyclic ring, such as piperidino, pyrrolidino, N-lower alkylpiperazino, morpholino, thiomorpholino and tetrahydro-2H,4H-1,3,6-dioxazocino or a fused heterocyclic ring system, e.g., quinolizidine.

The respective 2,3-dihydrobenz[d]isothiazole-1,1-dioxide and 2,3-dihydronaphtho[1,8-de]-1,2-thiazine-1,1-dioxide ring-closing moieties are illustrated below:

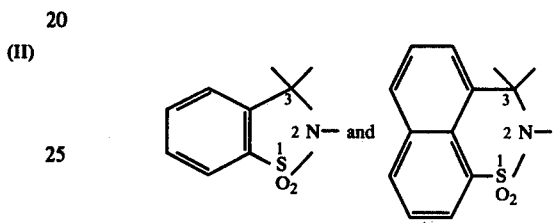

In a particularly preferred embodiment, the optical filter agent precursors of the present invention may be represented by the formula

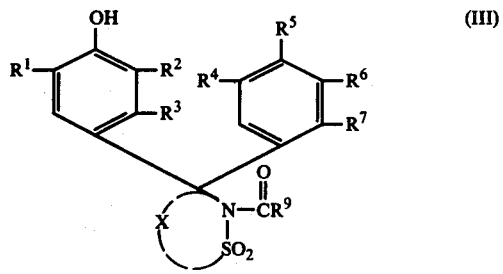

(III)

wherein $R^1$ and $R^2$ each are selected from hydrogen, alkyl, alkoxy, chloro and fluoro; $R^3$ is hydrogen, alkyl, alkoxy or hydroxy; $R^2$ and $R^3$ taken together represent the carbon atoms necessary to complete a fused benzene ring; $R^4$ and $R^6$ each are selected from hydrogen, alkyl, alkoxy, chloro and fluoro; $R^7$ is hydrogen, alkyl, alkoxy or hydroxy; $R^6$ and $R^7$ taken together represent the carbon atoms necessary to complete a fused benzene ring provided $R^2$ and $R^3$ are taken separately when $R^6$ and $R^7$ are taken together; $R^5$ is selected from hydrogen, hydroxy, alkyl, alkoxy, —N,N—(dialkyl)amino, —N,N—(w-$R^8$alkyl)$_2$amino wherein $R^8$ is hydroxy or halo, preferably chloro, —$NHCOCH_3$, piperidino, pyrrolidino, N-methylpiperazino, morpholino, thiomorpholino or tetrahydro-2H,4H-1,3,6-dioxazocino; $R^4$, $R^5$ and $R^6$ taken together represent the atoms necessary to complete a fused [ij]quinolizidine ring; X represents the atoms necessary to complete 2,3-dihydrobenz[d]isothiazole-1,1-dioxide or 2,3-dihydronaphtho[1,8-de]-1,2-thiazine-1,1-dioxide; and $R^9$ is methyl substituted with one halo group selected from chloro, bromo and fluoro or substituted with two of said halo groups, preferably the same, phenoxy substituted with at least one electron-withdrawing group, phenyl substituted in the ortho position with —$CH_2R^{10}$ wherein $R^{10}$ is chloro or bromo and —O(CH$_2$)$_2$Y wherein Y is an electron-withdrawing group having a positive sigma value above 0.60.

Usually, the alkyl and alkoxy substituents comprising R$^1$, R$^2$, R$^3$, R$^4$, R$^5$, R$^6$ and R$^7$ are lower alkyl having 1 to 4 carbon atoms, such as, methyl, ethyl, n-propyl, isopropyl and n-butyl and lower alkoxy having 1 to 4 carbon atoms, such as, methoxy, ethoxy, propoxy and butoxy. Also, the alkyl groups of the —N,N—(dialkyl)amino and —N,N—(w-R$^8$alkyl)$_2$amino substituents comprising R$^5$ usually are lower alkyl having 1 to 4 carbon atoms.

Illustrative electron-withdrawing groups, i.e., groups with a positive sigma value as defined by Hammett's Equation include halo, e.g., fluoro, chloro and bromo; cyano;

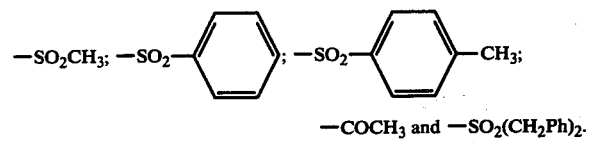

—COCH$_3$ and —SO$_2$(CH$_2$Ph)$_2$.

The sigma value for these and other groups have been reported by Eugen Muller, Methoden Der Organischen Chemie, Georg Thieme Verlag, Stuttgart, 1970, p. 78.

In a particularly preferred embodiment, X in formula (III) above represents the atoms necessary to complete 2,3-dihydrobenz[d]isothiazole-1,1-dioxide.

Because the colored optical filter agents provided by the above-described precursor compounds are converted to a substantially colorless product which is non-reversible to the colored filter agent regardless of changes in pH, the filter agent precursors of the subject invention find particular utility in diffusion transfer processes employing integral negative-positive film units. If desired, however, the subject compounds also may be used in conventional tray processing and in diffusion transfer processes where the negative and positive elements are separated for viewing the final image.

In carrying out the present invention, one or more optical filter agent precursors selected from those above are initially disposed in a layer or layers of a film unit in a position and in a concentration effective to prevent undesired exposure of a photosensitive material during processing in the presence of incident light. For example, the precursors may be disposed in a layer coextensive with one or both surfaces of the photosensitive layer(s) or disposed in a layer between the photosensitive layer(s) and the layer of image-receiving material, e.g., in a layer carried on the outermost photosensitive layer of the photosensitive element and/or in a layer coated over the image-receiving layer. The precursor(s) preferably is disposed in a layer of the film unit that is directly in contact with the layer of aqueous alkaline processing composition applied to process the film unit, e.g., in the outermost photosensitive layer, in the image-receiving layer or in a layer, preferably a preformed titania layer disposed between the outermost photosensitive layer and the image-receiving layer. In a particularly preferred embodiment, the precursor(s) are disposed in a layer coated over the photosensitive and/or image-receiving elements in diffusion transfer film units and particularly in an overcoat carried on the image-receiving layer.

In the present invention, the colorless precursor compounds may be associated with the photosensitive silver halide layers without having any adverse effects on the silver halide emulsions and normally are stable and inert therein. When the precursors are placed in other layers of the film unit, the materials comprising the layers should not adversely affect the precursor. When the precursor is present in a layer coated over the photosensitive and/or image-receiving layers, the polymeric binder employed should be essentially colorless, permeable to the aqueous alkaline processing composition and inert with respect to interacting deleteriously with the colorless precursor or the underlying layers and the compounds thereof. Though gelatin and other polymers may be used, an inert, processing composition permeable polymer found particularly useful as a binder for the colorless precursors are polymers of α-trifluoromethyl vinyl alcohol as described in U.S. Pat. No. 3,444,150 of H. C. Haas and N. W. Schuler issued May 13, 1969, particularly poly-α-trifluoromethyl vinyl alcohol.

Specific examples of compounds useful as colorless precursors for generating a colored compound which in turn is converted to a different colorless compound include:

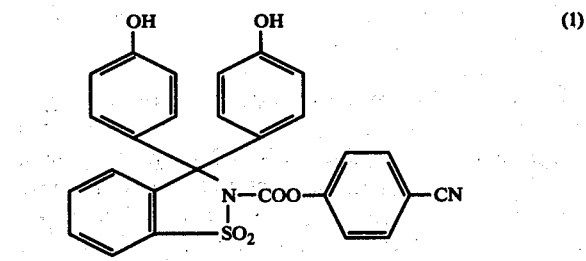

(1)

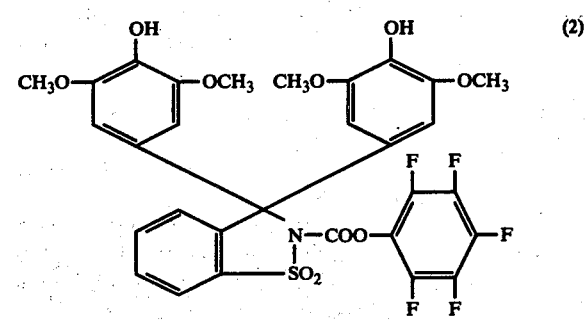

(2)

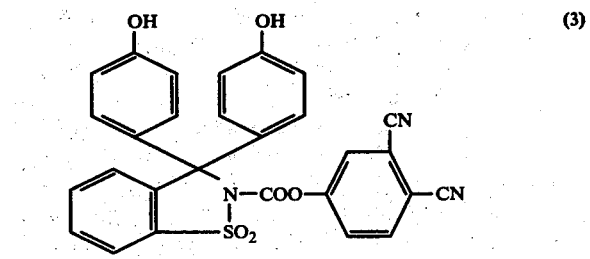

(3)

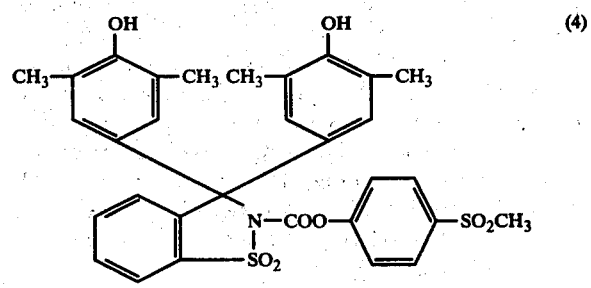

(4)

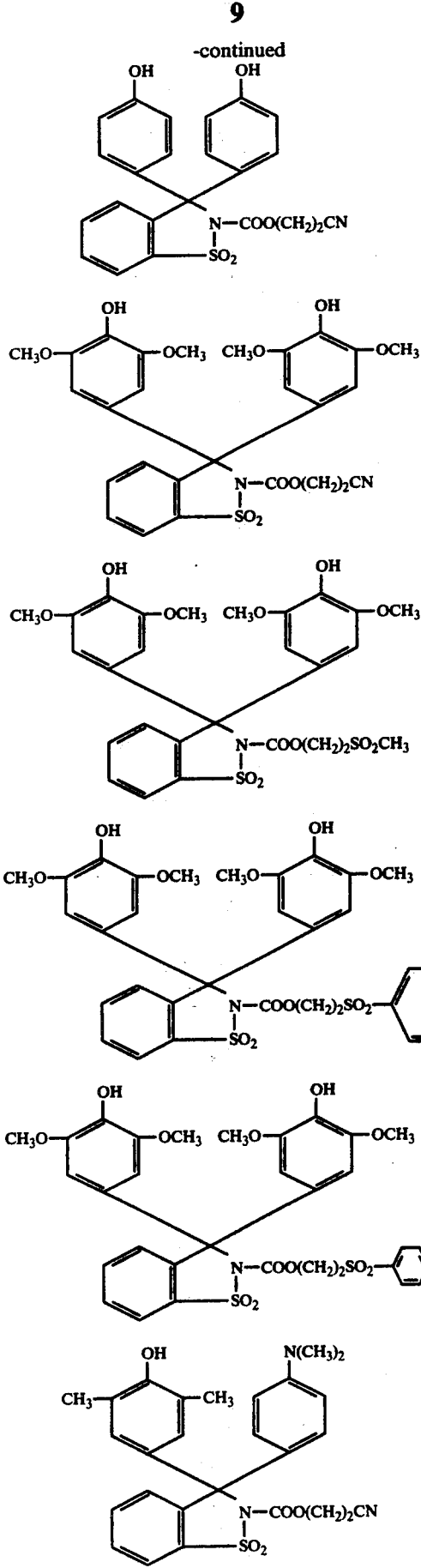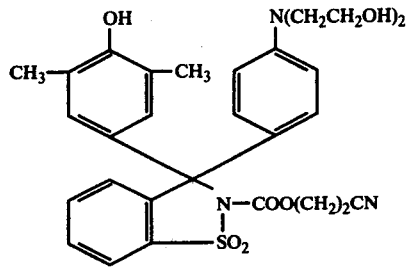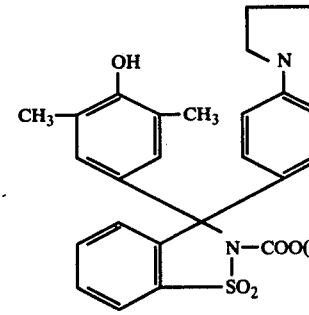

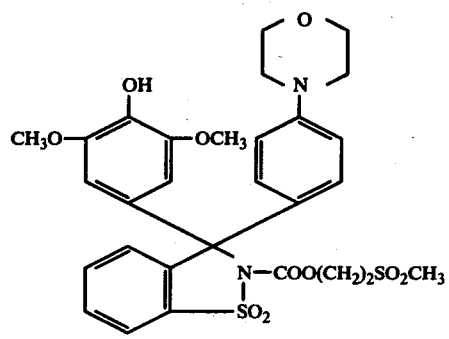
(16)
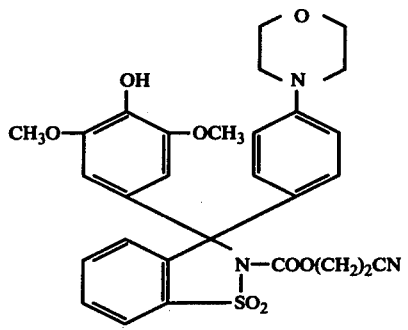
(17)
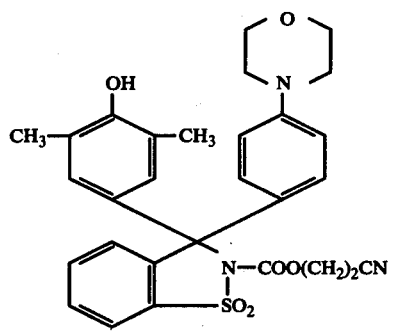
(18)
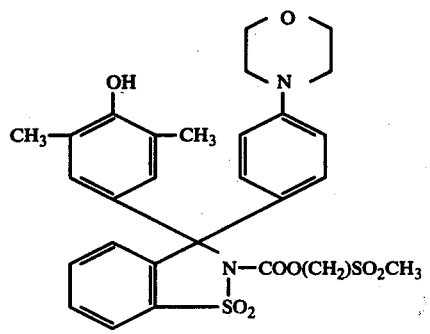
(19)
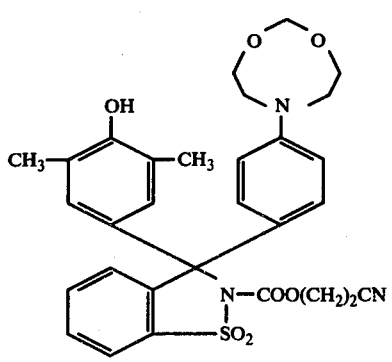
(20)
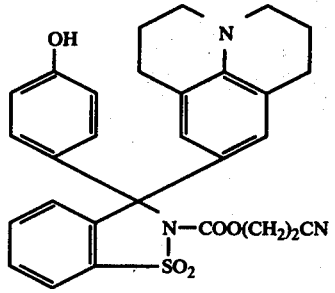
(21)
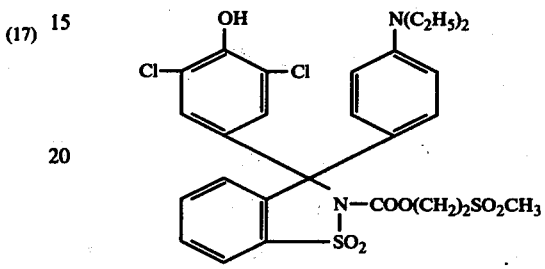
(22)
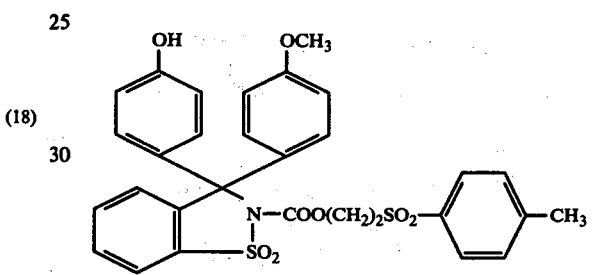
(23)
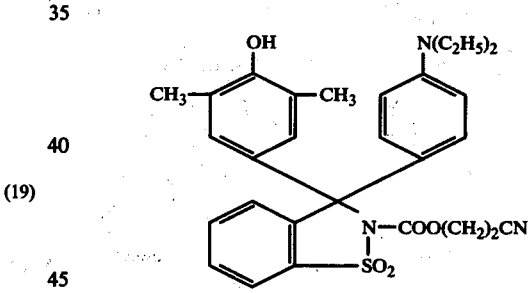
(24)
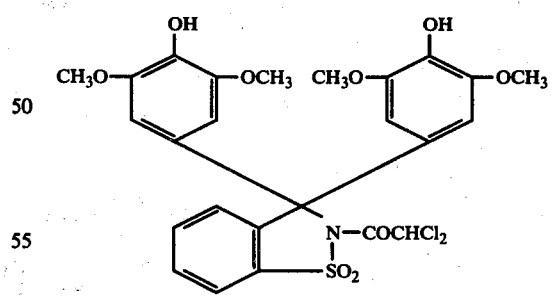
(25)
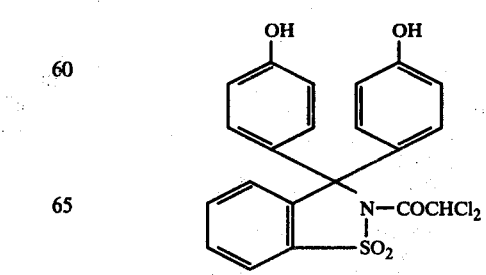
(26)

The colorless precursors of the present invention may be prepared by reacting (a) a 3-(4'-OP-1'-phenyl/4'-OP-1'-naphthyl)-3-(phenyl/naphthyl)-2,3-dihydrobenz[d]isothiazole-1,1-dioxide wherein P is a protecting group compatible with organometallic reagents and (b) an acylating agent, W-Z wherein W is chloro or bromo and Z is said carbonyl moiety in pyridine to give the corresponding 2-Z-3,3-disubstituted-2,3-dihydrobenz[d]isothiazole-1,1-dioxide. The N-acylated compound is then treated with weak acid to remove the protecting group(s) to yield the 3,3-disubstituted-2,3-dihydrobenz[- d]isothiazole-1,1-dioxide product. Optionally, the N-acylation step may be conducted by sequentially reacting (a) with an alkali metal hydride to form the corresponding N-alkali metal salt followed by reaction with the acylating agent. The compounds containing a 2,3-dihydronaphtho[1,8-de]-1,2-thiazine-1,1-dioxide as the ring-closing moiety are prepared by employing a 3-(4'-OP-1'-phenyl/4'-OP-1'-naphthyl-3-(phenyl/naphthyl)-2,3-dihydro naphtho[1,8-de]-1,2-thiazine-1,1-dioxide in the foregoing procedure. The above described method of synthesizing the compounds of the present invention forms the subject matter of commonly assigned copending U.S. patent application Ser. No. 836,010 of Stanley M. Bloom, Alan L. Borror and James W. Foley filed concurrently herewith.

The 3-(4'-OP-1'-phenyl/4'-OP-1'-naphthyl)-3-(phenyl/naphthyl)-2,3-dihydrobenz[d]isothiazole-1,1-dioxides employed as the intermediates, (a), in the above method may be synthesized by reacting a 3-(4'-OP-1'-phenyl/4'-OP-1'-naphthyl)-benz[d]isothiazole-1,1-dioxide and a phenyllithium or a naphthyllithium reagent as disclosed and claimed in commonly assigned copending U.S. patent application Ser. No. 836,008 of Alan L. Borror, Louis Cincotta, James W. Foley and Marcis M. Kampe filed concurrently herewith. The 3-(4'-OP-1'-phenyl/4'-OP-1'-naphthyl)benz[d]isothiazole-1,1-dioxide is prepared by converting a blocked 4-halophenol or a blocked 4-halo-1-naphthol to the corresponding Grignard or lithium reagent and then reacting this reagent with saccharin or saccharin pseudo-chloride. 3-(4'-OP-1'-phenyl/4'-OP-1'-naphthyl)-benz[d]isothiazole-1,1-dioxides form the subject matter of commonly assigned copending U.S. patent application Ser. No. 836,024 of Alan L. Borror, Louis Cincotta, Ernest W. Ellis, James W. Foley and Marcis M. Kampe filed concurrently herewith.

The method of aforementioned application Ser. No. 836,008 is useful in synthesizing intermediates for the subject compounds wherein the A and B moieties are either the same or different. Intermediates for the subject compounds wherein the A and B moieties are the same, i.e., identical, also may be prepared by reacting two equivalents of a blocked phenol (or blocked 1-naphthol) as a Grignard reagent with one equivalent of 3-chlorobenz[d]isothiazole-1,1-dioxide (or 3-chloronaphtho[1,8-de]-1,2-thiazine-1,1-dioxide) as disclosed and claimed in commonly assigned copending U.S. patent application Ser. No. 836,004 of Stanley M. Bloom, Alan L. Borror and James W. Foley filed concurrently herewith.

As discussed in the aforementioned applications, the protecting groups selected for preparing the blocked phenols or 1-naphthols and for blocking other substituents as may be necessary should be compatible with lithium and Grignard reagents and should protect the hydroxyl and other groups against reaction under conditions encountered in the synthesis of the starting materials and the intermediates and in the subsequent steps in the synthesis of the products. In addition, the protecting group(s) selected should be capable of being easily removed under neutral or weakly acid conditions to regenerate the hydroxyl and other groups and yield the desired product.

The compounds of formula III above wherein $R^9$ is methyl substituted with one or two halo groups form the subject matter of commonly assigned copending U.S. patent application Ser. No. 836,021 of Stanley M. Bloom, Alan L. Borror and James W. Foley filed concurrently herewith, and the compounds wherein $R^9$ is phenoxy, substituted with at least one electron-withdrawing group form the subject matter of commonly assigned copending U.S. patent application Ser. No. 836,009 of Stanley M. Bloom, of Alan L. Borror and James W. Foley also filed concurrently herewith. The compounds wherein $R^9$ is phenyl substituted in the ortho position with $CH_2R^{10}$ form the subject matter of commonly assigned copending U.S. patent application Ser. No. 836,005 of Stanley M. Bloom, Alan L. Borror and James W. Foley filed concurrently herewith, and the compounds wherein $R^9$ is $-O(CH_2)_2Y$ form the subject matter of commonly assigned copending U.S. patent application Ser. No. 835,998 of Stanley M. Bloom, of Alan L. Borror and James W. Foley also filed concurrently herewith.

For convenience, the specifications of aforementioned applications Ser. Nos. 836,004; 836,008; 836,024, 836,010; 836,021; 836,009; 836,005, and 835,998 are incorporated herein.

The synthesis of colorless precursors where the A and B moieties are the same is exemplified by the preparation of the compound having the formula

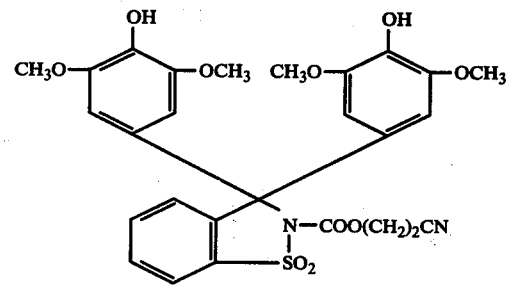

(a) 55 g. of 4-bromo-2,6-dimethoxy-methylenemethoxyphenyl ether was dissolved in 300 ml. of anhydrous tetrahydrofuran under a stream of nitrogen. The solution was cooled to −65° C. during which time some of the phenyl ether precipitated. To this was added 79 ml. of butyl-lithium (2.4M in hexane) at a range to keep the temperature below −50° C. The resulting solution was cooled to −65° C. and was stirred for 30 minutes. To this solution was added 19 g. of saccharin pseudo-chloride in two portions so as to keep the temperature below −40° C. The reaction solution was cooled to −65° C. and was stirred for 40 minutes. TLC showed one main spot on silica gel with 10 ml. ether/2 drops methanol. The reaction solution was poured into 2000 ml. of water and made acidic to pH 6. The mixture changed color from orange to yellow at this pH. The mixture was extracted two times with ether (2 liters) and the ether washed with water. The ether was dried over sodium sulfate and evaporated to leave a light yellow solid. The solid was recrystallized from 450 ml. of n-propanol to give 42 g. of 3,3-di(3',5'-dimethoxy-4'-methoxymethoxy-1'-phenyl)-2,3-dihydrobenz[d]isothiazole-1,1-dioxide as off-white crystals (melting range 151.5°-152.5° C.).

(b) The compound prepared in step (a) (27.0 g.) was dissolved in 125 ml. of dioxane at room temperature under nitrogen. To this solution was added 2.50 g. of NaH (57% oil dispersion) and the resulting dispersion stirred for 45 minutes. (Evolution of hydrogen was observed.) Then 8.0 ml. of $ClCOOCH_2CH_2CN$ was added and an exotherm resulted. The resulting reaction mixture was stirred for 3 hours. The initial yellow color disappeared and a white dispersion formed. The dispersion was poured into 2 liters of water, made neutral with dilute HCl and extracted with chloroform. The chloroform was washed with water, separated, dried over sodium sulfate, and evaporated to yield a white solid. The solid was stirred with ethyl ether, isolated by filtration, dried in vacuo, and crystallized from methanol. The white needles that formed were recovered by filtration to give the

derivative of 3,3-di(3',5'-dimethoxy-4'-methoxymethoxy-1'-phenyl)-2,3-dihydrobenz[d]isothiazole-1,1-dioxide.

(c) 3.7 g. of 3,3-di(3',5'-dimethoxy-4'-methoxymethoxy-1'-phenyl)-2-β-cyanocarbethoxy-2,3-dihydrobenz[d]isothiazole-1,1-dioxide prepared as in step (b) above was placed in 200 ml. of methanol and 2 drops of HCl were added. The resulting solution was refluxed and the reaction was followed by TLC on silica gel with ether. When TLC indicated that no more blocked compound remained, the reaction was discontinued and the methanol removed in vacuo to leave an egg-white solid (3.2 g.). This was dissolved in 80 ml. of 1,2-dichloroethane with heating and 80 ml. of petroleum ether was added with swirling. The solution was cooled and the light beige crystals that formed were collected and dissolved in 175 ml. of ethanol at reflux. The ethanol solution was allowed to cool in the refrigerator overnight and 2.7 g. of the title compound was collected as white needles (melting range 191°–193° C.).

The 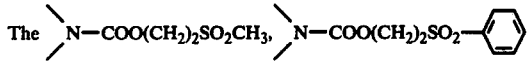

and 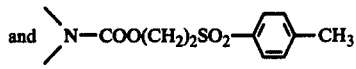

derivatives of 3,3-di(3',5'-dimethoxy-4'-methoxymethoxy-1'-phenyl)-2,3-dihydrobenz[d]isothiazole-1,1-dioxide were prepared by repeating the foregoing procedure and using as the acylating agents,

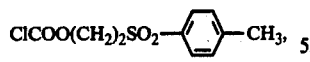

respectively. The N-acylated intermediates thus formed were then treated with dilute hydrochloric acid to remove the protecting groups and give the compounds of formulae 7, 8 and 9, respectively.

The methoxymethylation of 4-bromo-2,6-dimethoxyphenol was carried out as follows:

To a 3 liter flask was added 300 g. of $P_2O_5$ under nitrogen and 800 ml. of chloroform (previously dried over $P_2O_5$). The mixture was cooled to $-15°$ C. with a dry-ice acetone bath and then 50 g. of 4-bromo-2,6-dimethoxyphenol in 800 ml. of dimethoxymethane was added over a 25 minute period while maintaining the temperature at $-15°$ C. or below. To the resulting reaction mixture was added 1 ml. of conc. sulfuric acid and then the temperature was allowed to come to room tempreature. During this time, a tacky mass of $P_2O_5$ developed. The reaction mixture was stirred for 3 hours. TLC indicated that the reaction was complete. The chloroform was then decanted into 400 ml. of 10% aqueous sodium hydroxide, stirred well and the chloroform layer separated, washed with water, dried over $Na_2SO_4$ and evaporated to leave light tan crystals. n-Propanol was added to the crystalline residue, stirred and filtered to give 32.7 g. of the title compound as white crystals (melting range 98°–100° C.).

The compounds of formulae 5, 26, 29 and 30 were prepared according to the foregoing procedure except that

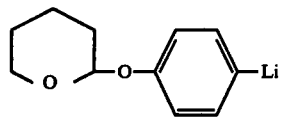

was reacted with the saccharin pseudo-chloride in step 1 and the product of step 1 was reacted with the appropriate acylating agent, namely, $ClCOO(CH_2)_2CN$, $ClCOCHCl_2$,

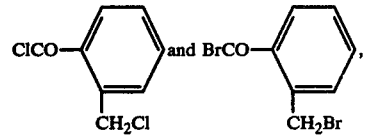

respectively and then treated with dilute acid to remove the protecting groups.

Tetrahydropyranylation of p-bromophenol to give the blocked starting phenol was carried out as follows:

To 10.5 ml. of dihydropyran containing 2 drops of conc. HCl was added 10.0 g. of p-bromophenol. (The reaction was exothermic; temperature rose to 35° C.). After the addition was completed, the colorless solution obtained was heated to 50° C. and allowed to cool with stirring for 1 hour. The solution was extracted with 20 ml. of ether and 10 ml. of 10% NaOH. The ether layer was dried over anhydrous $Na_2SO_4$ and evaporated under reduced pressure to leave an oil. 80 ml. of ethanol was added to the oil and the resulting ethanol solution was allowed to stand. The white crystals that formed were recovered by filtration and dried under vacuum to yield 7.3 g. of the blocked phenol. The mother liquor was concentrated to one-half its original volume and cooled. More crystals formed which were isolated to yield an additional 2.1 g. of blocked phenol.

The synthesis of colorless precursors where the A and B moieties are different is exemplified by the preparation of the compound having the formula:

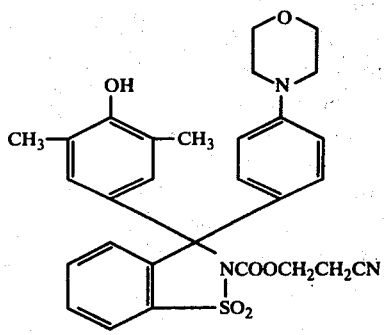

(a') N-(p-bromophenyl)morpholine (0.4 g.) was added to 20 ml. of tetrahydrofuran (THF) and the solution cooled to −65° C. To the solution was added 0.69 ml. of 2.4M butyllithium in hexane with stirring and stirring was continued for 1 hour. (After 15 minutes the solution became cloudy and a white precipitate formed.) To this solution was added 0.5 g. of 3-(3',5'-dimethyl-4'-methoxymethoxy-1'-phenyl)benz[d]isothiazole-1,1-dioxide in 2 ml. THF at −65° C. under nitrogen. The resulting reaction mixture was a clear orange-yellow solution. The reaction mixture was stirred for 1 hour, poured into 100 ml. of water, made acidic with conc. hydrochloric acid (pH 6), and extracted with ether. The ether was dried over Na₂SO₄ and evaporated leaving an oil. The oil was taken up in ligroin (boiling range 30°-60° C.) and refluxed for 1 hour. The white solid that formed was collected to give 0.7 g. of 3-(3',5'-dimethyl-4'-methoxymethoxy-1'-phenyl)-3-(4"-N-morpholinyl-1"-phenyl)-2,3-dihydrobenz[d]isothiazole-1,1-dioxide having the formula:

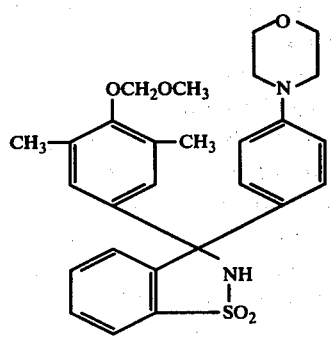

(b') The compound prepared in step (a') (0.7 g.) was placed in 20 ml. of pyridine under nitrogen and 0.15 ml. of β-cyanoethylchloroformate (ClCO₂CH₂CH₂CN) was added to the pyridine solution. The resulting reaction solution was stirred 1 hour, warmed gently and then poured into 100 ml. of water and extracted with chloroform. The chloroform was dried over Na₂SO₄, evaporated and the solid that formed was extracted with ligroin (boiling range 30°-60° C.). The solid obtained was the N-acylated compound, 3-(3',5'-dimethyl-4'-methoxymethoxy-1'-phenyl)-3-(4"-N-morpholinyl-1"-phenyl)-2-(β-cyanocarbethoxy)-2,3-dihydrobenz[-d]isothiazole-1,1-dioxide having the formula:

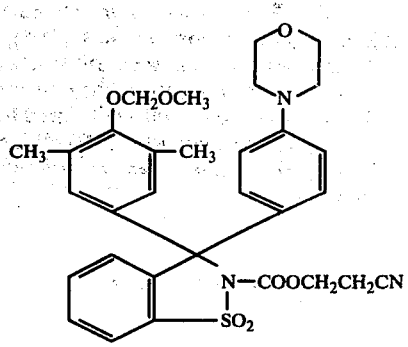

(c') The compound obtained in step (b') was then dissolved in methanol, made acidic with conc. hydrochloric acid and refluxed 1 hour. TLC from ether on silica gel showed 4 spots. The methanol solution was evaporated to leave 0.6 g. of solid. 200 mg. of solid in ether was placed on silica gel 1000 plates and the dark band was removed after drying plates. Acetone was used to remove the N-acylated product from the silica gel. The acetone was removed, ether added and the solution refluxed. The white solid that formed was recovered by filtration to give the title compound.

The 3-(3',5'-dimethyl-4'-methoxymethoxy-1'-phenyl)benz[d]isothiazole-1,1-dioxide having the formula:

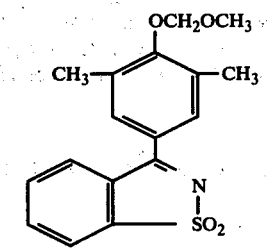

used in step (a') above was prepared as follows:

(i) Into a 2 liter three neck flask, fitted with a mechanical stirrer, nitrogen inlet and a dropping funnel, was placed 700 ml. of dry chloroform. The flask was immersed in an ice-water bath. Powdered phosphorus pentoxide (300.0 g.) was added to the vigorously stirred, cold chloroform. To this mixture was added over a 1 hour period a solution of 4-bromo-2,6-dimethylphenol (201.0 g.) in 400 ml. of dry dimethoxymethane. During this time the phosphorus pentoxide powder fused into an amorphous mass and stirring became difficult. TLC analysis (9:1 petroleum ether-ethyl acetate on silica gel) indicated that much unreacted starting phenol was still present. The temperature of the reaction mixture was allowed to rise to about 25° C. Additional 50 g. increments of phosphorus pentoxide were added to the stirred reaction mixture every 30–45 minutes until TLC analysis indicated the absence of starting phenol. The organic layer was decanted, washed with two 250 ml. portions of aqueous 10% sodium hydroxide and dried over calcium sulfate. The solvent was removed under reduced pressure leaving a pale yellow oil which was distilled from 25 g. of anhydrous potassium carbonate to give 220.0 g. of 4-bromo-2,6-dimethylmethylenemethoxyphenyl ether as a colorless oil (boiling point 112° C. and 0.5 mm Hg).

(ii) 4-Bromo-2,6-dimethyl-methylenemethoxyphenyl ether (85.04 g.; 0.347 mole) was dissolved in approximately 800 ml. of tetrahydrofuran. The solution was cooled to −75° C. under a nitrogen blanket, and 2.4M n-butyllithium in hexane (144.8 ml; 0.346 mole) was added dropwise. Addition was completed within a 2 hour period giving a white slurry.

(iii) Saccharin (61.2 g; 0.334 mole) was dissolved in 600 ml. of dry tetrahydrofuran, and the solution was cooled to approximately −75° C. 2.4M n-butyllithium in hexane (130.4 ml; 0.311 mole) was slowly added dropwise to the cooled solution under a nitrogen blanket. The temperature was not allowed to rise above −70° C. Addition was completed in about 90 minutes, giving a clear, very pale yellow solution.

(iv) The yellow solution obtained in step (iii) was slowly added (over a 3 hour period) to the white slurry obtained in step (ii) while keeping the temperature at −70° C. During this time the solids disappear giving a clear, caramel colored reaction mixture that first tends to darken with time and then gradually lightens. The reaction mixture was allowed to come to room temperature overnight and then was treated with 36.0 g. of ammonium chloride in 250 ml. of water, while cooling in an ice-water bath. The organic portion was decanted and dried over anhydrous calcium sulfate. The solvent was removed under reduced pressure to give a pink colored oil that became solid on standing in open air. The solid was recrystallized twice from 1-propanol, washed with a 60:40% mixture of petroleum ether-tetrahydrofuran and dried under vacuum to give 68.0 g. of the title compound as a white, crystalline solid.

3-(3',5'-dimethyl-4'-methoxymethoxy-1'-phenyl)-benz[d]isothiazole-1,1-dioxide also was prepared as follows:

Dry tetrahydrofuran (10–15 ml.) was added to magnesium turnings (0.20 g.) under nitrogen. A solution of 4-bromo-2,6-dimethyl-methylenemethoxyphenyl ether (2.0 g.) in tetrahydrofuran (30 ml.) was added gradually to the magnesium turnings with stirring and heating. After about twenty minutes of external heating to reflux, a self-sustaining reaction was observed. The remaining solution of phenyl ether was then added at a rate to maintain a comfortable reaction. Refluxing with external heating was continued after addition was complete and after one hour, the solution was cooled to room temperature and held under nitrogen. A solution of saccharin pseudo-chloride (1.89 g.) in tetrahydrofuran (40 ml.) was cooled to −78° C. and the previously prepared solution of magnesium bromide reagent was added dropwise to the pseudo-chloride solution under nitrogen. The resulting reaction mixture was stirred cold for about 2 hours and then stirred at room temperature overnight. The reaction mixture was then cooled in an ice water bath and treated with saturated aqueous ammonium chloride solution. The aqueous solution was extracted with chloroform several times and the combined chloroform extracts washed with water and dried over anhydrous sodium sulfate followed by drying over anhydrous calcium sulfate. Upon removing the chloroform, a colorless oil was obtained which was extracted several times with small portions of light petroleum ether to leave behind a pale yellow tacky tar. The yellow tar was treated with ether leaving behind an off-white solid. The off-white solid was dissolved in a small amount of chloroform, treated with carbon black and filtered through Celite. Upon removing the solvent, the title compound was obtained as an off-white solid which was dried under vacuum in the presence of $P_2O_5$. Yield 0.520 g.

3-chlorobenz[d]isothiazole-1,1-dioxide (saccharin pseudo-chloride) was prepared as follows:

35 g. of saccharin and 43.7 g. of $PCl_5$ were heated at 170° C. for 1½ hours during which time complete solution occurred and $POCl_3$ began to reflux. The $POCL_3$ was removed at reduced pressure to leave a crystalline residue. Diethyl ether was added to the crystalline residue and stirred well. The title compound was recovered as white crystals, 12.5 g. (melting range 146°–147° C.).

The N-(p-bromophenyl)morpholine having the formula

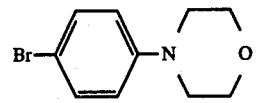

used in step (a') above was prepared as follows:

25 g. of N-phenylmorpholine was dissolved in 200 ml. of carbon tetrachloride and stirred well. To this was added all at once 27.2 g. of N-bromosuccinimide. There was an exotherm to 45° C. The reaction solution was stirred until the temperature began to decrease and then was heated to reflux for 3 hours. TLC on silica gel with 3/2 petroleum ether/ether indicated that the reaction was complete. The reaction solution was then cooled, the succinimide removed by filtration and the solution evaporated to yield a yellow solid. The solid was dissolved in 250 ml. of ethanol and cooled to give 22 g. of the title compound as white crystals.

The β-cyanoethylchloroformate having the formula $(CNCH_2CH_2COOCl)$ used in step (b') above was prepared as follows:

To 100 ml. of dry benzene, cooled in an ice bath, was added phosgene gas until 34.0 g. was collected. Hydroxyacrylonitrile (20.2 g.) was added to the cooled phosgene solution. (The temperature rose slightly to approximately 8° C.) The resulting heterogeneous mixture was cooled to 3° C. with stirring, and pyridine (22.6 g.) in 25 mls. of benzene was added dropwise. Heat was evolved, and the temperature was not allowed to rise above 10° C. Very vigorous stirring was maintained until solid began to form. After about 1 hour, the reaction mixture was stirred at approximately 5° C. for 15 minutes, then allowed to come to 15° C.–20° C. and stirred for another 15 minutes. The reaction mixture was then cooled to 5° C. and 26 ml. of ice water was added in increments. The solids dissolved with liberation of heat and evolution of gas. The temperature was not allowed to rise above 15° C. over the next 15–20 minutes. The reaction mixture was then stirred at room temperature for 2 hours, the benzene layer decanted and dried over anhydrous $Na_2SO_4$, followed by drying over anhydrous $CaSO_4$. The solvent was removed under reduced pressure to yield an almost colorless oil which was redistilled under vacuum at a boiling range of 68.5°–70.5° C. (pot temperature 98°–103° C.) to yield 18.2 g. of the title compound as a colorless oil.

The compounds of formulae 11–17, 19 and 20 were prepared according to the foregoing procedure by reacting the selected 3-(4'-OP-1'-phenyl)-benz[d]isothiazole-1,1-dioxide with the selected substituted phenyl lithium reagent followed by N-acylation with the appropriate acylating agent in pyridine and finally removing the protecting group in weak acid to yield the product.

In carrying out the present invention, the colorless optical filter agent precursor(s) are selected to provide upon contact with the alkaline processing composition, colored optical filter agent(s) exhibiting spectral absorption of radiation at the wavelengths to which the silver halide layer or layers are sensitive. Commensurate with the spectral sensitivity range of the photosensitive element, one or more of the subject filter agent precursors may be employed to provide the necessary protection from post-exposure fogging by incident light. Also, the optical filter agents and filter agent precursors of the present invention may be used in combination with optical filter agent(s) of a different type, for example, with the aforementioned pH-sensitive optical filter agents, particularly those disclosed in the previously cited U.S. Pat. Nos. 3,647,437; 3,702,244; and 3,702,245.

The quantity of the light-absorbing material required to provide protection of the photosensitive material will vary with the process being performed and the conditions (light level) under which it is expected that the process will be performed, and may be readily determined by routine tests. The presence of a light-reflecting layer between the source of light and the light-absorbing material will materially reduce the required quantity of light-absorbing material, and will also reduce the amount of heat generated within the film unit by absorption of incident light during processing. General guides for determining suitable concentrations of light-absorbing materials may be found in the previously mentioned U.S. Pat. No. 3,647,437.

Image dye-providing materials which may be employed generally may be characterized as either (1) initially soluble or diffusible in the processing composition but are selectively rendered non-diffusible in an imagewise pattern as a function of development; or (2) initially insoluble or non-diffusible in the processing composition but which are selectively rendered diffusible or provide a diffusible product in an imagewise pattern as a function of development. These materials may be complete dyes or dye intermediates, e.g., color couplers. The requisite differential in mobility or solubility may, for example, be obtained by a chemical action such as a redox reaction or a coupling reaction.

As examples of initially soluble or diffusible materials and their application in color diffusion transfer, mention may be made of those disclosed, for example, in U.S. Pat. Nos. 2,774,668; 2,968,554; 2,983,606; 3,087,817; 3,185,567; 3,230,082; 3,345,163; and 3,443,943. As examples of initially non-diffusible materials and their use in color transfer systems, mention may be made of the materials and systems disclosed in U.S. Pat. Nos. 3,185,567; 3,443,939; 3,443,940; 3,227,550; 3,227,552 and Published U.S. Application B-351,673. Both types of image dye-providing substances and film units useful therewith also are discussed in the aforementioned U.S. Pat. No. 3,647,437 to which reference may be made.

In any of these systems, multicolor images are obtained by employing a film unit containing at least two selectively sensitized silver halide layers each having associated therewith an image dye-providing material exhibiting desired spectral absorption characteristics. The most commonly employed elements of this type are the so-called tripack structures employing blue-, green- and a red-sensitive silver halide layers having associated therewith, respectively, a yellow, a magenta and a cyan image dye-providing material, as disclosed in U.S. Pat. No. 3,345,163 issued Oct. 3, 1967 to Edwin H. Land and Howard G. Rogers.

A particularly useful system for forming color images by diffusion transfer is that described in U.S. Pat. No. 2,983,606, employing dye developers (dyes which are also silver halide developing agents) as the image dye-providing materials. In such systems, a photosensitive element comprising at least one silver halide layer having a dye developer associated therewith (in the same or in an adjacent layer) is developed by applying an aqueous alkaline processing composition. Development of exposed silver halide results in oxidation of the dye developer to provide an oxidation product which is appreciably less diffusible than the unreacted dye developer, thereby providing an imagewise distribution of diffusible dye developer in terms of unexposed areas of the silver halide layer, which imagewise distribution is then transferred, at least in part, by diffusion, to a dyeable stratum to impart thereto a positive dye transfer image. Multicolor images may be obtained with a photosensitive element having two or more selectively sensitized silver halide layers and associated dye developers, a tripack structure of the type described above in various patents including the aforementioned U.S. Pat. Nos. 2,983,606 and 3,345,163 being especially suitable for accurate color recordation or original subject matter.

In such color diffusion transfer systems, color transfer images are obtained by exposing a photosensitive element, sometimes referred to as a "negative component", comprising at least a light-sensitive layer, e.g., a gelatino silver halide emulsion layer, having an image dye-providing material associated therewith in the same or in an adjacent layer, to form a developable image; developing this exposed element with a processing composition to form an imagewise distribution of a diffusible image dye-providing material; and transferring this imagewise distribution, at least in part, by diffusion, to a superposed image-receiving layer, sometimes referred to as a "positive component", comprising at least a dyeable stratum to provide a color transfer image. The negative and positive components initially may be carried on separate supports which are brought together during processing and thereafter retained together as the final integral negative-positive reflection print, or they may initially comprise a unitary structure, e.g., integral negative-positive film units wherein the negative and positive components are part of a photosensitive laminate or they may otherwise be physically retained together in superposed relationship prior to, during and after image formation. (Procedures for forming such film units wherein the positive and negative components are temporarily laminated together prior to exposure are described, for example, in U.S. Pat. No. 3,652,281 to Albert J. Bachelder and Frederick J. Binda and in U.S. Pat. No. 3,652,282 to Edwin H. Land, both issued Mar. 28, 1972.) In either instance, the positive component is not removed from the negative component for viewing purposes. The preferred film units comprise a plurality of essential layers including a negative component comprising at least one light-sensitive silver halide and associated dye image-providing material and a positive component comprising a dyeable stratum. These components may be laminated together or otherwise secured together in physical juxtaposition. Film units intended to provide multicolor images comprise two or more selectively sensitized silver halide layers each having associated therewith an appropriate image dye-providing material providing an image dye having spectral absorption characteristics substantially complementary to the light by which the associated silver halide is exposed. The most commonly employed negative components for forming multicolor images are of the tripack structure and contain blue-, green- and red-sensitive silver halide layers each having associated therewith in the same or in a contiguous layer a yellow, a magenta and a cyan image dye-providing material respectively. Interlayers or spacer layers may, if desired, be provided between the respective silver halide layers and associated image dye-providing materials or between other layers. In addition to the aforementioned essential layers, such film units further include means for providing a reflecting layer between the dyeable stratum and the negative component in order to mask effectively the silver image or images formed as a function of development of the silver halide layer or layers and also to mask image dye-providing material which is not transferred, thereby providing a background, preferably white, for viewing the color image formed in the dyeable stratum, without separation, by reflected light. This reflecting layer may comprise a preformed layer of a reflecting agent included in the film unit or the reflecting agent may be provided after photoexposure, e.g., by including the reflecting agent in the processing composition. The dye transfer image is then viewable through a dimensionally stable protective layer or support. Most preferably another dimensionally stable layer or support, which may be transparent or opaque, is positioned on the opposed surface of the essential layers so that the aforementioned essential layers are between a pair of dimensionally stable layers or support members, one of which is transparent to permit viewing therethrough of the color transfer image. A rupturable container of known description contains the requisite processing composition and is adapted upon application of pressure to release its contents for development of the exposed film unit, e.g., by distributing the processing composition in a substantially uniform layer between a pair of predetermined layers. In film units of the type illustrated in the Figure, a processing composition containing a white pigment may be distributed between the dyeable stratum and the negative component to provide the light-reflecting layer.

In lieu of having the light-reflecting pigment in the processing composition, the light-reflecting pigment used to mask the photosensitive strata and to provide the requisite background for viewing the color transfer image formed in the receiving layer may be present initially in whole or in part as a preformed layer in the film unit. As an example of such a preformed layer, mention may be made of that disclosed in U.S. Pat. Nos. 3,615,421 issued Oct. 26, 1971 and in 3,620,724 issued Nov. 16, 1971, both in the name of Edwin H. Land. The reflecting agent may be generated in situ as is disclosed in U.S. Pat. Nos. 3,647,434 and 3,647,435, both issued Mar. 7, 1972 to Edwin H. Land.

The dye developers (or other image dye-providing substances) are preferably selected for their ability to provide colors that are useful in carrying out subtractive color photography, that is, the previously mentioned cyan, magenta and yellow. They may be incorporated in the respective silver halide emulsion or, in the preferred embodiment, in a separate layer behind the respective silver halide emulsion. Thus a dye developer may, for example, be in a coating or layer behind the respective silver halide emulsion and such a layer of dye developer may be applied by use of a coating solution containing the respective dye developer distributed, in a concentration calculated to give the desired coverage of dye developer per unit area, in a film-forming natural, or synthetic, polymer, for example, gelatin, polyvinyl alcohol, and the like, adapted to be permeated by the processing composition.

Dye developers, as noted above, are compounds which contain the chromophoric system of a dye and also a silver halide developing function. By "a silver halide developing function" is meant a grouping adapted to develop exposed silver halide. A preferred silver halide development function is a hydroquinonyl group. Other suitable developing functions include ortho-dihydroxyphenyl and ortho-and para-amino substituted hydroxyphenyl groups. In general, the development function includes a benzenoid developing function, that is, an aromatic developing group which forms quinonoid or quinone substances when oxidized.

The image-receiving layer may comprise one of the materials known in the art, such as polyvinyl alcohol, gelatin, etc. It may contain agents adapted to mordant or otherwise fix the transferred image dye(s). Preferred materials comprise polyvinyl alcohol or gelatin containing a dye mordant such as poly-4-vinylpyridine, as disclosed in U.S. Pat. No. 3,148,061, issued Sept. 8, 1964 to Howard C. Haas. If the color of the transferred image dye(s) is affected by changes in pH, the pH of the image layer may be adjusted to provide a pH affording the desired color.

In the various color diffusion transfer systems which have previously been described and which employ an aqueous alkaline processing fluid, it is well known to employ an acid-reacting reagent in a layer of the film unit to lower the environmental pH following substantial dye transfer in order to increase the image stability and/or to adjust the pH from the first pH at which the image dyes are diffusible to a second (lower) pH at which they are not. For example, the previously mentioned U.S. Pat. No. 3,415,644 discloses systems wherein the desired pH reduction may be effected by providing a polymeric acid layer adjacent the dyeable stratum. These polymeric acids may be polymers which contain acid groups, e.g., carboxylic acid and sulfonic acid groups, which are capable of forming salts with alkali metals or with organic bases; or potentially acid-yielding groups such as anhydrides or lactones. Preferably the acid polymer contains free carboxyl groups. Alternatively, the acid-reacting reagent may be in a layer adjacent the silver halide most distant from the image-receiving layer, as disclosed in U.S. Pat. No. 3,573,043 issued Mar. 30, 1971 to Edwin H. Land. Another system for providing an acid-reacting reagent is disclosed in U.S. Pat. No. 3,576,625 issued Apr. 27, 1971 to Edwin H. Land.

An inert interlayer or spacer layer may be and is preferably disposed between the polymeric acid layer and the dyeable stratum in order to control or "time" the pH reduction so that it is not premature and interfere with the development process. Suitable spacer or "timing" layers for this purpose are described with particularity in U.S. Pat. Nos. 3,362,819; 3,419,389; 3,421,893; 3,455,686; and 3,575,701.

While the acid layer and associated spacer layer are preferably contained in the positive component employed in systems wherein the dyeable stratum and photosensitive strata are contained on separate supports, e.g., between the support for the receiving element and the dyeable stratum; or associated with the dyeable stratum in those integral film units, e.g., on the side of the dyeable stratum opposed from the negative components, if desired they may be alternatively or additionally associated with the photosensitive strata, as is disclosed, for example, in U.S. Pat. Nos. 3,362,821 and 3,573,043. In film units such as those described in the aforementioned U.S. Pat. Nos. 3,594,164 and 3,594,165, they also may be contained on the spreader sheet employed to facilitate application of the processing fluid.

As is now well known and illustrated, for example, in the previously cited patents, the liquid processing composition referred to for effecting multicolor diffusion transfer processes comprises at least an aqueous solution of an alkaline material, for example sodium hydroxide, potassium hydroxide, and the like, and preferably possessing a pH in excess of 12, and most preferably includes a viscosity-increasing compound constituting a film-forming material of the type which, when the composition is spread and dried, forms a relatively firm and relatively stable film. The preferred film-forming materials disclosed comprise high molecular weight polymers such as polymeric, water-soluble ethers which are inert to an alkaline solution such as, for example, a hydroxyethyl cellulose or sodium carboxymethyl cellulose. Other film-forming materials or thickening agents whose ability to increase viscosity is substantially unaffected if left in solution for a long period of time are also known to be capable of utilization. As stated, the film-forming material is preferably contained in the processing composition in such suitable quantities as to impart to the composition a viscosity in excess of 100 cps. at a temperature of approximately 24° C. and preferably in the order of 100,000 cps. to 200,000 cps. at that temperature.

FIG. 1 illustrates a preferred embodiment of this invention wherein an opaque film support 10 carries, in order, a layer 12 of a cyan dye developer, a layer 14 of a red-sensitive silver halide emulsion, an interlayer 16, a layer 18 of a magenta dye developer, a layer 20 of a green-sensitive silver halide emulsion, an interlayer 22, a layer 24 of a yellow dye developer, and a layer 26 of a blue-sensitive silver halide emulsion. A second support 32 (transparent) carries a polymeric acid layer 34, a spacer or timing layer 36, and an image-receiving layer 38. Over the latter layer there is provided an essentially colorless layer 28 of at least one optical filter agent precursor of the present invention in a polymeric binder. Following photoexposure through the transparent support 32 and the layers carried thereon, the container 30 is ruptured and the processing composition contained therein is distributed between the opposing surfaces of layers 26 and 28. Contact by the alkaline processing composition is effective to cause the precursor to generate a colored optical filter agent. The processing composition in the container 30 includes a light-reflecting material, e.g., titanium dioxide, and a light-reflecting layer is thereby provided between layers 26 and 28. After a predetermined suitable period, the polymeric acid layer 34 is permeated by alkali and the pH is reduced to a predetermined level. Within said period before pH reduction the colored optical filter agent is discharged by forming a new compound which is colorless and non-reversible to said colored filter agent or said precursor. The final multicolor transfer image in the image-receiving layer 38 is viewed through the transparent support 32 against a white background provided by the titanium dioxide. Suitable means, e.g., binder tape, not shown, may be provided to secure the various layers in fixed relationship prior to, during and after photoexposure and processing. Such film units may be ejected out of a camera into ambient light.

As discussed above, by positioning the optical filter agent precursor(s) in a layer adjacent to, i.e., contiguous with the layer of processing composition being applied, there is minimum delay between application of the alkaline solution and contact with the precursor(s) to effect generation of the colored optical filter agent. Also, by positioning the precursor(s) in this manner, larger amounts of the colored optical filter agent become admixed with the light-reflecting agent in the processing composition to provide enhanced protection of the photosensitive layer(s) by virtue of the synergistic effect between the colored optical filter agent(s) and the light-reflecting agent as discussed in aformentioned U.S. Pat. No. 3,647,437. Because the colored optical filter agent(s) generate a permanently colorless product after a predetermined time in contact with the alkaline processing composition, the final position of the colorless product is not critical, especially in film units where the negative and positive components are retained together as part of a permanent laminate.

The following example is given for purposes of illustration only.

EXAMPLE

A multicolor photosensitive element using, as the cyan, magenta and yellow dye developers.

cyan:

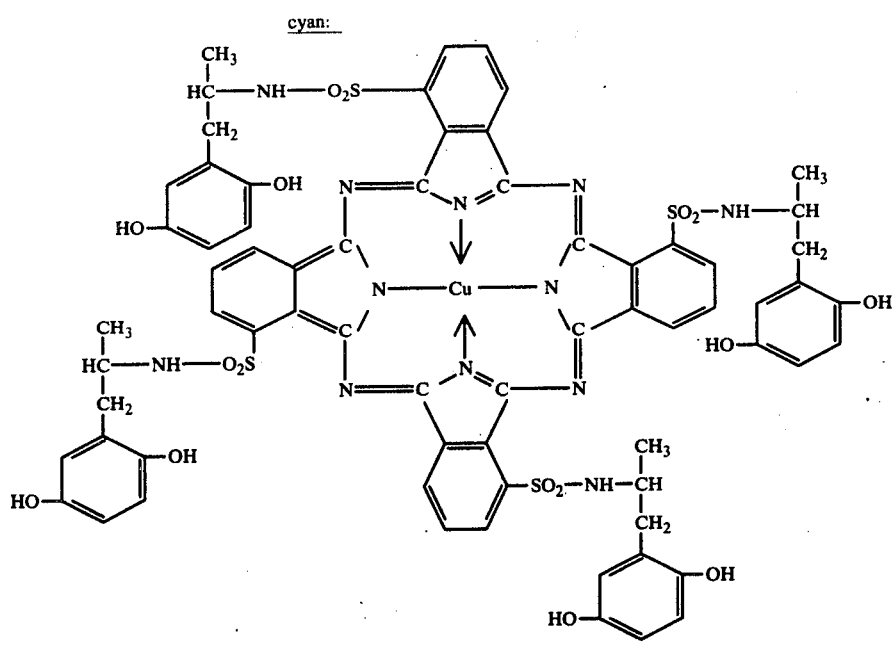

magenta:

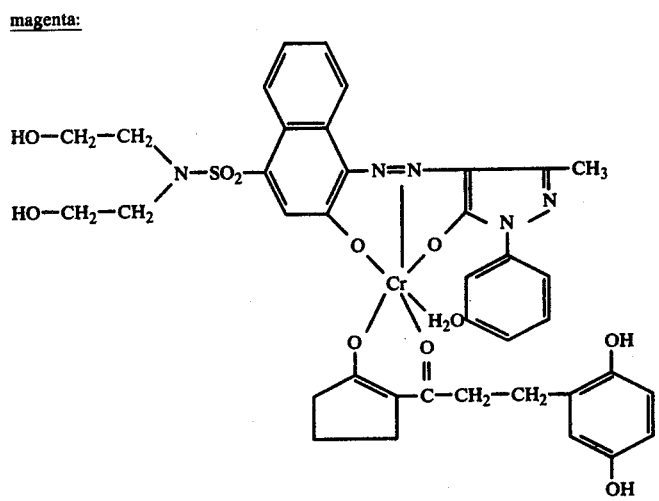

yellow:

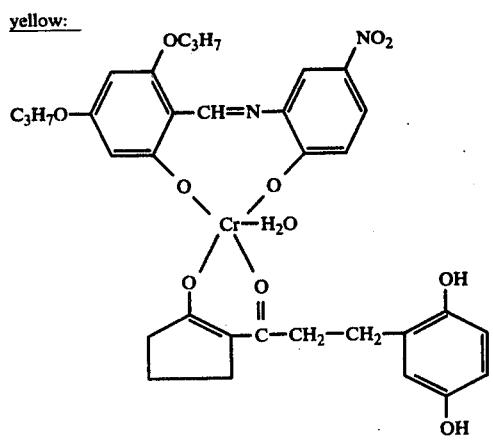

was prepared by coating a gelatin-subcoated 4 mil opaque polyethylene terephthalate film base with the following layers:

1. a layer of cyan dye developer dispersed in gelatin and coated at a coverage of 57.8 mgs./ft.$^2$ of dye and 105 mgs./ft.$^2$ of gelatin, plus 4'-methylphenyl hydroquinone coated at a coverage of 5.25 mgs./ft.$^2$ and 2-phenylbenzimidazole coated at a coverage of 21 mgs./ft.$^2$;

2. a red-sensitive gelatino silver iodobromide emulsion coated at a coverage of 84 mgs./ft.$^2$ of silver and 109 mgs./ft.$^2$ of gelatin;

3. a layer of 60-30-4-6 tetrapolymer of butylacrylate, diacetone acrylamide, styrene and methacrylic acid and polyacrylamide coated at a coverage of 559 mgs./ft.$^2$ of the copolymer and 29.4 mgs./ft.$^2$ of polyacrylamide;

4. a layer of magenta dye developer dispersed in gelatin and coated at a coverage of 60 mgs./ft.$^2$ of dye and 42 mgs./ft.$^2$ of gelatin; and about 21 mgs./ft.$^2$ of 2-phenylbenzimidazole;

5(a). a green-sensitive gelatino silver iodobromide emulsion possessing a mean silver halide particle size of about 1.05 m$\mu$ coated at a coverage of about 30 mgs./ft.$^2$ of silver and 36 mgs./ft.$^2$ of gelatin;

(b). a green-sensitive gelatino silver iodobromide emulsion possessing a mean silver halide particle size of about 1.20 m$\mu$ coated at a coverage of about 36 mgs./ft.$^2$ of silver and 43.2 mgs./ft.$^2$ of gelatin;

6. a layer containing the tetrapolymer referred to above in layer 3 plus polyacrylamide coated at a coverage of about 225 mgs./ft.$^2$ of tetrapolymer and 19.9 mgs./ft.$^2$ of polyacrylamide; and also containing 3 mgs./ft.$^2$ of succindialdehyde; 7. a layer of yellow dye developers dispersed in gelatin and coated at a coverage of 72 mgs./ft.$^2$ of dye and 33.8 mgs./ft.$^2$ of gelatin; and also containing 19.4 mgs./ft.$^2$ of 2-phenylbenzimidazole;

8. a blue-sensitive gelatino silver iodobromide emulsion coated at a coverage of 119 mgs./ft.$^2$ of silver and 62 mgs./ft.$^2$ of gelatin; and also containing 22 mgs./ft.$^2$ of 4'-methylphenylhydroquinone; and 9. a layer of gelatin coated at a coverage of 40 mgs./ft.$^2$ of gelatin and also containing carbon black coated at a coverage of 4 mgs./ft.$^2$ A transparent 4 mil polyethylene terephthalate film base was coated, in succession, with the following layers to form an image-receiving component:

1. as a polymeric acid layer, the partial butyl ester of polyethylene/maleic anhydride copolymer at a coverage of about 2,500 mgs./ft.$^2$;

2. a timing layer containing a 14:1 ratio of a 60-30-4-6 tetrapolymer of butylacrylate, diacetone acrylamide, styrene and methacrylic acid and polyvinylalcohol at a coverage of 500 mgs./ft.$^2$;

3. a polymeric image-receiving layer containing a 2:1 mixture, by weight, of polyvinyl alcohol and poly-4-vinylpyridine, at a coverage of 300 mgs./ft.$^2$ The image-receiving component was coated, over the polymeric image-receiving layer, with an acetone solution of poly-$\alpha$-trifluoromethyl vinyl alcohol and the compound of formula 19 to provide layer 4, an essentially continuous and colorless layer of said optical filter agent precursor compound at a coverage of 30 mgs./ft.$^2$ of precursor and 30 mgs./ft.$^2$ of polymer.

The aqueous alkaline processing composition comprised the following in % by weight.

| | |
|---|---|
| Water | 49.28 |
| Potassium hydroxide | 5.39 |
| Carboxymethyl hydroxyethyl cellulose | 1.79 |
| Benzotriazole | 0.77 |
| 4-aminopyrazolo-3,4-D-pyrimidine | 0.20 |
| 6-methyluracil | 0.21 |
| N-2-hydroxyethyl-N,N',N'-triscarboxymethyl-ethylene diamine | 0.81 |
| bis(2-aminoethyl)sulfide | 0.02 |
| Polyethylene glycol (mol. wt. 6000) | 0.50 |
| Titanium dioxide | 38.10 |
| Colloidalsilica aqueous dispersion (30% SiO$_2$) | 1.68 |
| N-phenethyl-$\alpha$-picolinium bromide | 1.25 |

To the above composition was added 0.32 gms. of the pH-sensitive dye of the formula

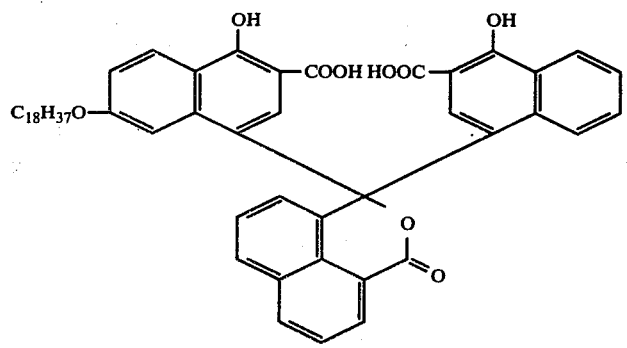

The photosensitive element was exposed to a multicolor stepwedge, the image-receiving element superposed on the exposed photosensitive element, and a rupturable container of the processing composition attached. This assembly was passed between a pair of pressure rolls so that a layer approximately 0.0026" thick of the processing composition was distributed between the gelatin overcoat layer 9 of the photosensitive element and the layer of optical filter agent precursor coated over the image-receiving element. The resulting laminate was brought into room light (approximately 75 foot-candles) and maintained intact to provide a multicolor integral negative-positive reflection print.

Using identical film units, the above procedure was repeated except that the resulting laminates were brought into simulated sunlight of 5,000 foot-candles and 10,000 foot-candles, respectively.

The test multicolor dye transfer images prepared in the manner described above were compared to control images prepared identically with the exception that the optical filter agent precursor was omitted from layer 4 of the image-receiving component. Such a comparison clearly revealed the effectiveness of the optical filter agent generated by the precursor compound in preventing post-exposure fogging during processing in the presence of light as reflected by the maximum densities obtained which are set forth below.

| Positive Transfer Image Density ($D_{max}$) | | |
|---|---|---|
| Surface Illumination | Control | Test |
| (a) 75 ft.-candles | | |
| Red | 1.75 | 1.70 |
| Green | 2.01 | 1.93 |
| Blue | 1.84 | 1.85 |
| (b) 5,000 ft.-candles | | |

| Positive Transfer Image Density ($D_{max}$) | | |
| --- | --- | --- |
| Surface Illumination | Control | Test |
| Red | 1.51 | 1.76 |
| Green | 0.85 | 1.90 |
| Blue | 1.21 | 1.82 |
| (c) 10,000 ft.-candles | | |
| Red | 1.36 | 1.75 |
| Green | 0.57 | 1.90 |
| Blue | 1.02 | 1.81 |

The colored optical filter agent generated from precursor compounds possessing a

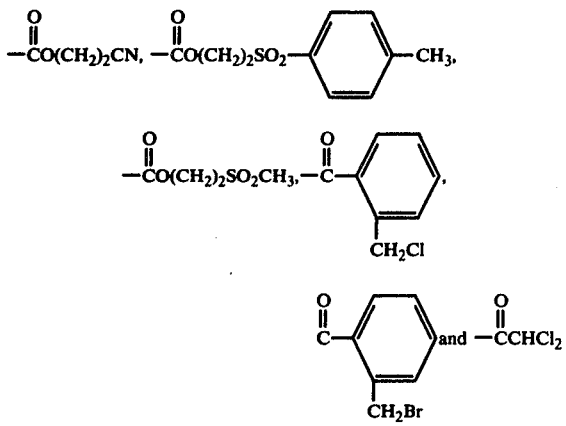

moiety in the 2-position of the benz[d]isothiazole-1,1-dioxide ring have a half-life (T½) in approximately 1N NaOH of 30 seconds, 14 seconds, 7 seconds, 13 seconds, 8.5 seconds and 95–120 minutes, respectively. By T½ is meant the time measured for one-half of the colored species to decolorize.

Figure 2:
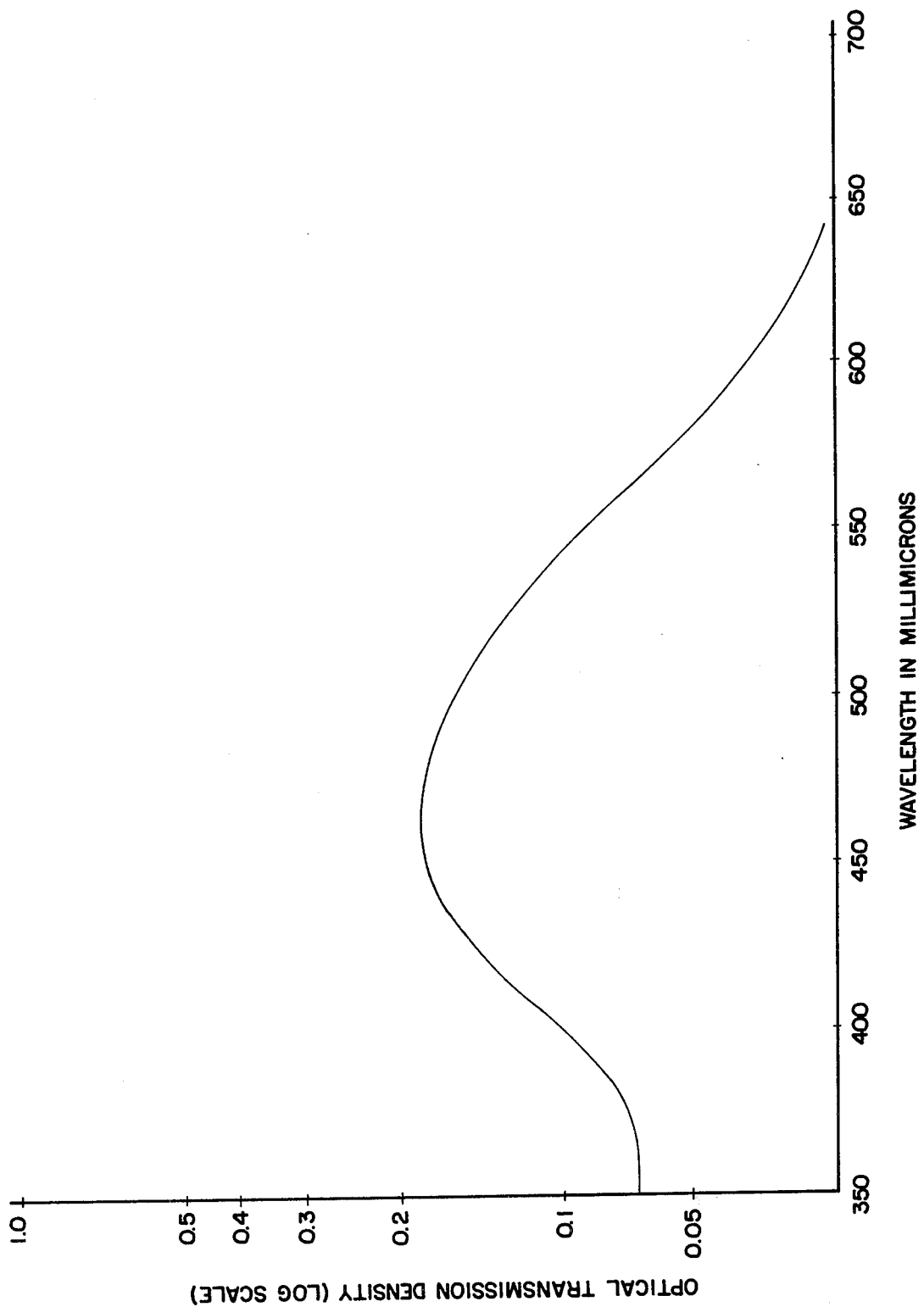
FIGS. 2 and 3 are graphic illustrations of the spectral absorption characteristics of the colored optical filter agents formed in basic solution by the precursor compounds of the present invention represented hereinafter by the formulae designated (19) and (6). These graphs represent the optical transmission density, i.e., absorbance of the respective filter agents measured on a logarithm scale over the wavelength range of 350 nm. to 700 nm.
Figure 3:
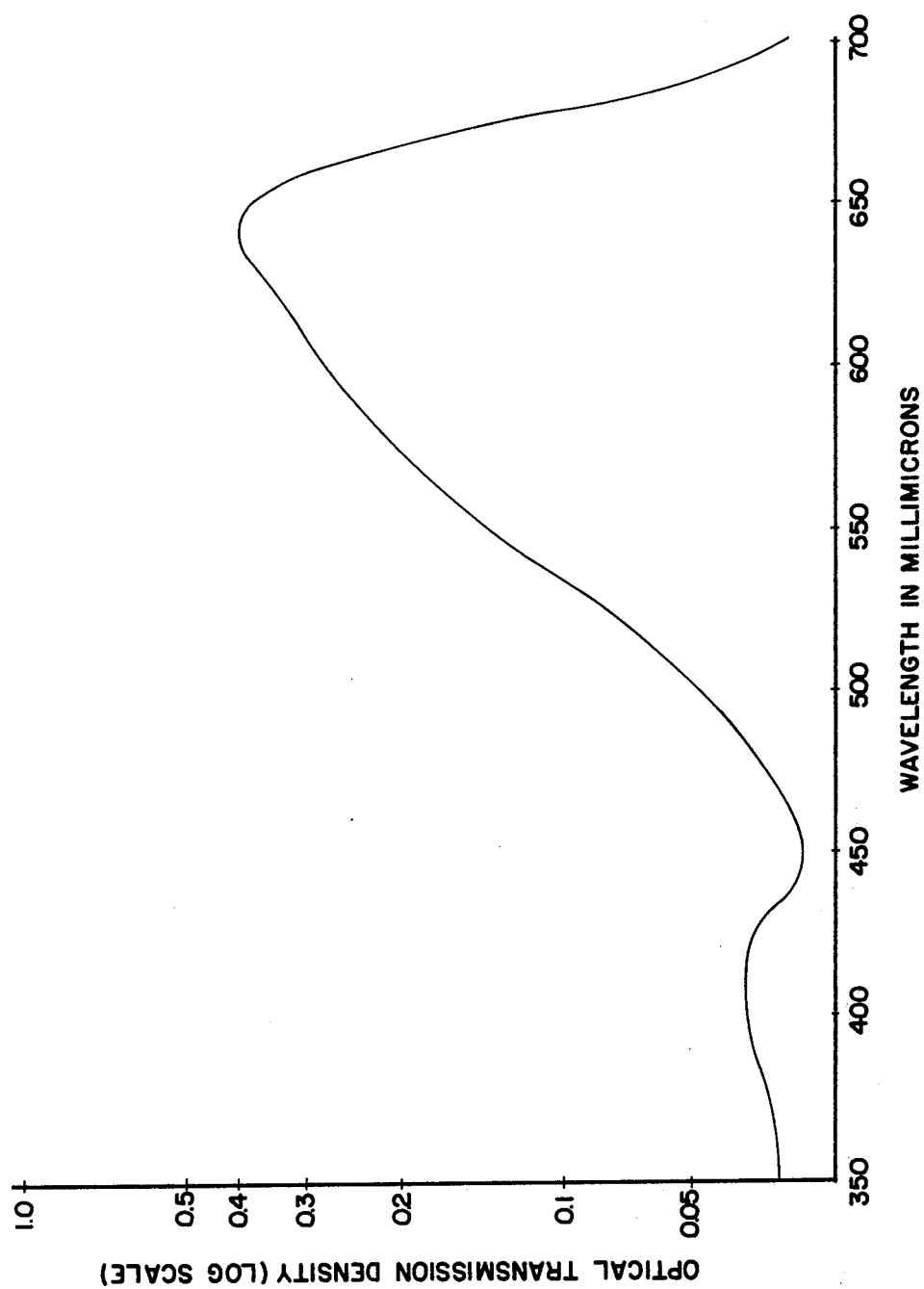

The spectral absorption characteristics of the colored optical filter agents generated by the 2-COCH₃ analogs of compounds (19) and (6) are graphically illustrated in FIGS. 2 and 3, respectively, wherein the absorption curves were obtained by placing said compounds in aqueous 1N sodium hydroxide to generate said colored filter agents.

It will be understood that dye transfer images which are neutral or black-and-white instead of multicolor may be obtained by use of a mixture of dyes of the appropriate colors, the transfer of which may be controlled by a single layer of silver halide, in accordance with known techniques. It is also to be understood that "direct positive" silver halide emulsions may also be used, depending upon the particular dye image-providing substances employed and whether a positive or negative color transfer image is desired, and that the precursors of this invention may be employed in film units designed to have the image-receiving layer separated from the developed photosensitive layer(s) after processing has been completed.

The provision of a short dark time, e.g., five to fifteen seconds, following application of the processing composition will permit development to be completed under ambient light levels using smaller concentrations of optical filter agents than would be required for light protection if there was no such initial dark time.

While in the preferred embodiment as shown in FIG. 1 the layer 28 of the optical filter agent precursor is coated over the image-receiving element, it will be understood that it is within the scope of this invention to coat said layer 28 over layer 26 of the photosensitive element. In the latter embodiment, it is preferred to also use a pH-sensitive optical filter agent(s) in the processing composition.

Although the invention has been primarily described in connection with color diffusion transfer processes, it will be understood that the invention also may be employed in diffusion transfer processes which provide a silver transfer image. Silver transfer processes in which optical filter agents may be employed are described in detail in the aforementioned U.S. Pat. No. 3,647,437 to which reference may be made. Thus, for example, an optical filter agent precursor layer such as layer 28 of FIG. 1 in this application may be coated over the silver receptive layer 118 of FIG. 10 of said U.S. Pat. No. 3,647,437.

As noted earlier, the system of converting a colorless precursor to a colored compound which in turn is converted to a different colorless compound may be utilized in other applications. As one example thereof, this system may be utilized to provide a verification or validation system, e.g., for documents. Furthermore, the color(s) generated and the T½ for the decolorization thereof may be varied to permit validation systems unique to a particular type of document or purpose for which the document is used. Further, since the colorless precursor is initially present it may be provided in an imagewise manner, i.e., to provide a particular pattern, code or symbol when the colored compound has been formed, thus providing additional validation potential as well as use-related variations.

Since certain changes may be made in the above product and process without departing from the scope of the invention herein involved, it is intended that all matter contained in the above description shall be interpreted as illustrative and not in a limiting sense.

What is claimed is:

1. A process which comprises the steps of exposing a photosensitive film unit comprising a plurality of layers including at least a support carrying a photosensitive silver halide layer, and a substantially colorless optical filter agent precursor activated at an alkaline pH to form a colored optical filter agent disposed in at least one of said layers in a position effective to prevent undesired exposure of said photosensitive layer during processing in the presence of incident light, said colored optical filter agent after a predetermined time at a predetermined alkaline pH forming a substantially colorless compound different from and non-reversible to either said precursor or said filter agent by pH change, contacting said photosensitive layer and said precursor with an aqueous processing composition having an alkaline pH at least as high as said predetermined alkaline pH to initiate development and effect formation of said optical filter agent and maintaining the pH of said processing composition in contact with said optical filter agent at least as high as said predetermined alkaline pH at least until said colored optical filter agent has been converted to said colorless compound, said colorless optical filter agent precursor being a compound of the formula

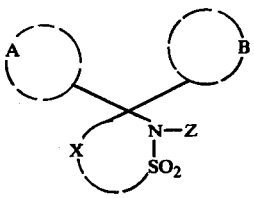

wherein A is a 4'-hydroxy-1'-phenyl moiety or a 4'-hydroxy-1'-naphthyl moiety; B is a phenyl moiety or a naphthyl moiety, provided A is said 4'-hydroxy-1'-phenyl moiety when B is said naphthyl moiety; X represents the carbon atoms necessary to complete a ring-closing moiety selected from a 2,3-dihydrobenz[d]isothiazole-1,1-dioxide moiety and a 2,3-dihydronaphtho[1,8-de]-1,2-thiazine-1,1-dioxide moiety; and Z is a carbonyl moiety containing a

group bonded to the N atom of said ring-closing moiety that undergoes an irreversible cleavage reaction in alkaline solution above a predetermined alkaline pH.

2. A process as defined in claim 1 wherein said predetermined pH is above about pH 10.

3. A process as defined in claim 1 including the step of separating said processing composition from contact with said photosensitive film unit subsequent to development and conversion of said colored optical filter agent to said colorless compound.

4. A process as defined in claim 1 wherein said colorless optical filter agent precursor is disposed in a processing composition permeable layer carried on the surface of said photosensitive silver halide layer opposite said support.

5. A process as defined in claim 1 which comprises, in combination, the steps of:
(a) exposing a photosensitive film unit comprising a plurality of layers including an opaque support carrying a photosensitive silver halide layer having associated therewith an image-providing material, an image-receiving layer adapted to receive solubilized image-providing material diffusing thereto, and said colorless optical filter agent precursor disposed in at least one of said layers in a position effective to prevent undesired exposure of said photosensitive layer during processing in the presence of incident light;
(b) contacting said photosensitive layer and said precursor with an aqueous processing composition having an alkaline pH at least as high as said predetermined pH;
(c) effecting thereby development of said silver halide layer and formation of said optical filter agent;
(d) maintaining the pH of said processing composition in contact with said optical filter agent at least as high as said predetermined alkaline pH at least until said colored optical filter agent has been converted to said colorless compound;
(e) forming as a result of said development, an imagewise distribution of diffusible image-providing material as a function of the point-to-point degree of exposure; and
(f) transferring, by diffusion, at least a portion of said imagewise distribution of diffusible image-providing material to said layer adapted to receive said material to provide a transfer image thereto.

6. A process as defined in claim 5 which includes the step of maintaining said film unit intact subsequent to said processing.

7. A process as defined in claim 6 wherein said processing composition includes a silver halide solvent and said transfer image is an image in silver.

8. A process as defined in claim 7 wherein said A of said colorless optical filter agent precursor is a 4'-hydroxy-1'-phenyl moiety.

9. A process as defined in claim 6 wherein said photosensitive film unit includes, in combination, at least a first support carrying in order at least one silver halide layer, each said silver halide layer having associated therewith a dye image-providing material; a dyeable image-receiving layer; means for providing a light-reflecting layer between said image-receiving layer and said silver halide layer(s) to mask said silver halide layer(s) after development thereof and to provide a white background for viewing a transfer image in said image-receiving layer; a transparent support through which said transfer image in said image-receiving layer may be viewed; a rupturable container providing an aqueous alkaline processing composition for developing said silver halide layer(s) after photoexposure and for forming said transfer image in said image-receiving layer; and said colorless optical filter agent precursor positioned in the silver halide layer outermost from said first support, in said image-receiving layer or in a processing composition permeable layer positioned between said outermost silver halide layer and said image-receiving layer or in a combination of said layers, said alkaline processing composition having an alkaline pH at least as high as said predetermined pH.

10. A process as defined in claim 9 wherein said dye image-providing material is selected from image dyes and image dye intermediates.

11. A process as defined in claim 10 wherein each said dye image-providing material is a dye.

12. A process as defined in claim 11 wherein each said dye is a dye developer.

13. A process as defined in claim 9 wherein said silver halide layer(s) are adapted to be exposed through said transparent support.

14. A process as defined in claim 9 wherein said means providing a light-reflecting layer comprise a white pigment dispersed in said processing composition, and said processing composition is contained in a rupturable container positioned to distribute said processing composition containing said pigment between said image-receiving layer and said silver halide layer(s).

15. A process as defined in claim 9 wherein said colorless optical filter agent precursor is coated over said image-receiving layer.

16. A process as defined in claim 9 wherein said silver halide layer(s), in sequence, are a red-sensitive silver halide emulsion layer, a green-sensitive silver halide emulsion layer; and a blue-sensitive silver halide emulsion layer; said silver halide emulsion layers having associated therewith, respectively, a cyan dye developer, a magenta dye developer and a yellow dye developer.

17. A process as defined in claim 16 wherein said support carrying said silver halide emulsion layer(s) is opaque.

18. A process as defined in claim 17 wherein said layers are held in fixed relationship between said supports prior to and during exposure.

19. A process as defined in claim 18 wherein said film unit includes means to reduce the pH of a layer of said processing composition from a first pH to a second pH.

20. A process as defined in claim 19 wherein said means to reduce the pH comprises a layer of an acid-reacting reagent positioned between said transparent support and said image-receiving layer.

21. A process as defined in claim 20 wherein said colorless optical filter agent precursor is coated over said image-receiving layer.

22. A process as defined in claim 21 wherein said A of said colorless optical filter agent precursor is a 4'-hydroxy-1'-phenyl moiety.

23. A process as defined in claim 21 wherein said processing composition includes an additional organic optical filter agent which is colored at the pH of said processing composition, said optical filter agent being adapted to be rendered colorless by reducing said pH.

24. A photographic product for forming a diffusion transfer image within a permanent laminate including at least one developed silver halide layer, said photographic product comprising, in combination, an image-receiving layer; at least one silver halide emulsion, each said silver halide emulsion having associated therewith an image-providing substance; means providing a light-reflecting layer between said image-receiving layer and said silver halide emulsion(s) to mask said silver halide emulsion(s) after development thereof and to provide a white background for viewing a transfer image in said image-receiving layer; a transparent support through which said transfer image in said image-receiving layer may be viewed; a rupturable container providing an aqueous alkaline processing composition for developing said silver halide emulsion(s) after photoexposure and for forming said transfer image in said image-receiving layer; said product including a substantially colorless optical filter agent precursor activated at an alkaline pH to form a colored optical filter agent, said colored optical filter agent after a predetermined time at a predetermined alkaline pH forming a substantially colorless compound different from and non-reversible to either said precursor or said filter agent by pH change, said colorless optical filter agent precursor being positioned in the silver halide emulsion next adjacent to said image-receiving layer, in said image-receiving layer, in a processing composition permeable layer positioned between said silver halide emulsion next adjacent to said image-receiving layer and said image-receiving layer or in a combination of said layers, said aqueous alkaline processing composition having an alkaline pH at least as high as said predetermined pH, said colorless optical filter agent precursor being a compound of the formula

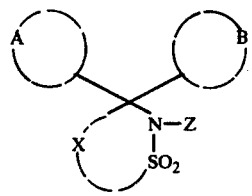

wherein A is a 4'-hydroxy-1'-phenyl moiety or a 4'-hydroxy-1'-naphthyl moiety; B is a phenyl moiety or a naphthyl moiety, provided A is said 4'-hydroxy-1'-phenyl moiety when B is said naphthyl moiety; X represents the carbon atoms necessary to complete a ring-closing moiety selected from a 2,3-dihydrobenz[d]isothiazole-1,1-dioxide moiety and a 2,3-dihydronaphtho[1,8-de]-1,2-thiazine-1,1-dioxide moiety; and Z is a carbonyl moiety containing a

group bonded to the N atom of said ring-closing moiety that undergoes an irreversible cleavage reaction in alkaline solution above a predetermined alkaline pH.

25. A photographic product as defined in claim 24 wherein each said image-providing substance is an image dye-providing substance selected from the group consisting of image dyes and image dye intermediates.

26. A photographic product as defined in claim 25 wherein each said image dye-providing substance is a dye.

27. A photographic product as defined in claim 26 wherein each said dye is a dye developer.

28. A photographic product as defined in claim 25 wherein each said image dye-providing substance is an intermediate for an image dye.

29. A photographic product as defined in claim 24 wherein said silver halide emulsion(s) are adapted to be exposed through said transparent support.

30. A photographic product as defined in claim 24 wherein said processing composition includes a silver halide solvent and said transfer image is an image in silver.

31. A photographic product as defined in claim 30 wherein said colorless optical filter agent precursor is coated over said image-receiving layer.

32. A photographic product as defined in claim 24 wherein said A of said colorless optical filter agent precursor is a 4'-hydroxy-1'-phenyl moiety.

33. A photographic product as defined in claim 24 wherein said means providing a light-reflecting layer comprise a white pigment dispersed in said processing composition, and said processing composition is contained in a rupturable container positioned to distribute said processing composition containing said pigment between said image-receiving layer and said silver halide emulsion(s).

34. A photographic product as defined in claim 33 wherein said colorless optical filter agent precursor is coated over said image-receiving layer.

35. A photographic product comprising a first support; a red-sensitive silver halide emulsion; a green-sensitive silver halide emulsion; and a blue-sensitive silver halide emulsion; said silver halide emulsions having associated therewith, respectively, a cyan dye developer, a magenta dye developer and a yellow dye developer; an image-receiving layer for receiving image dyes transferred thereto by diffusion as a function of exposure and development of said silver halide emulsion layer; a second support which is transparent and through which said image-receiving layer may be viewed; a rupturable container releasably holding aqueous alkaline processing composition adapted, upon distribution between predetermined layers of said film to develop said silver halide emulsions and to effect the formation of a transfer image in dye in said image-receiving layer, said processing composition also being adapted to provide a permanent laminate including said developed silver halide emulsions and said image-receiving layer; and means providing a light-reflecting layer between said image-receiving layer and said silver halide emulsions effective to provide a white background for viewing said transfer image and for masking said developed silver halide emulsions; said product including a substantially colorless optical filter agent precursor activated at an alkaline pH to form a colored optical filter agent, said colored optical filter agent after a predetermined time at a predetermined alkaline pH forming a substantially colorless compound different from and non-reversible to either said precursor or said filter agent by pH change, said colorless optical filter agent precursor being positioned in the silver halide emulsion next adjacent to said image-receiving layer, in said image-receiving layer, in a processing composition permeable layer positioned between said silver halide layer next adjacent to said image-receiving layer and said image-receiving layer or in a combination of said layers, said alkaline processing composition having an alkaline pH at least as high as said predetermined pH, said colorless optical filter agent precursor being a compound of the formula

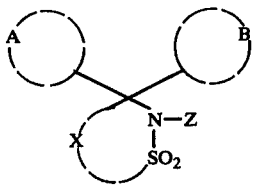

wherein A is a 4'-hydroxy-1'-phenyl moiety or a 4'-hydroxy-1'-naphthyl moiety; B is a phenyl moiety or a naphthyl moiety, provided A is said 4'-hydroxy-1'-phenyl moiety when B is said naphthyl moiety; X represents the carbon atoms necessary to complete a ring-closing moiety selected from a 2,3-dihydrobenz isothiazole-1,1-dioxide moiety and a 2,3-dihydronaphtho-1,2-thiazine-1,1-dioxide moiety; and Z is a carbonyl moiety containing a

group bonded to the N atom of said ring-closing moiety that undergoes an irreversible cleavage reaction in alkaline solution above a predetermined alkaline pH.

36. A photographic product as defined in claim 35 wherein said means for providing a light-reflecting layer comprises a preformed layer of a white pigment.

37. A photographic product as defined in claim 35 wherein said means for providing a light-reflecting layer comprises a white pigment dispersed in said processing composition.

38. A photographic product as defined in claim 35 wherein said first support is opaque.

39. A photographic product as defined in claim 35 wherein said transparent support is a polyester.

40. A photographic product as defined in claim 39 wherein said polyester is polyethylene terephthalate.

41. A photographic product as defined in claim 38 wherein said opaque support is polyethylene terephthalate.

42. A photographic product as defined in claim 35 wherein said transparent support and said image-receiving layer comprise a separate element adapted to be brought into superposed relationship with said silver halide emulsions.

43. A photographic product as defined in claim 35 wherein said layers are held in fixed relationship between said supports prior to and during exposure.

44. A photographic product as defined in claim 43 wherein said fixed relationship is provided by a binder tape along at least two parallel sides of said product.

45. A photographic product as defined in claim 35 wherein the blue-sensitive silver halide emulsion layer is between said image-receiving layer and said other silver halide emulsion layers.

46. A photographic product as defined in claim 35 wherein the blue-sensitive silver halide emulsion layer is between said first support and said other silver halide emulsion layers, and said first support is transparent.

47. A photographic product as defined in claim 35 including means to reduce the pH of a layer of said processing composition from a first pH to a second pH.

48. A photographic product as defined in claim 47 wherein said means to reduce the pH comprises a layer of an acid-reacting reagent positioned between said transparent support and said image-receiving layer.

49. A photographic product as defined in claim 48 wherein said acid-reacting reagent is a polymer.

50. A photographic product as defined in claim 35 wherein said processing composition includes an additional organic optical filter agent which is colored at the pH of said processing composition, said optical filter agent being adapted to be rendered colorless by reducing said pH.

51. A photosensitive element comprising a plurality of layers including at least a support carrying a photosensitive silver halide emulsion layer and a substantially colorless optical filter agent precursor activated at an alkaline pH to form a colored optical filter agent disposed in at least one of said layers in a position effective to prevent undesired exposure of said photosensitive layer during processing in the presence of incident light, said colored optical filter agent after a predetermined time at a predetermined alkaline pH forming a substantially colorless compound different from and non-reversible to either said precursor or said filter agent by pH change, said colorless optical filter agent precursor being a compound of the formula

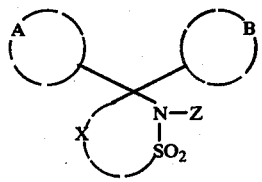

wherein A is a 4'-hydroxy-1'-phenyl moiety or a 4'-hydroxy-1'-naphthyl moiety; B is a phenyl moiety or a naphthyl moiety, provided A is said 4'-hydroxy-1'-phenyl moiety when B is said naphthyl moiety; X represents the carbon atoms necessary to complete a ring-closing moiety selected from a 2,3-dihydrobenz isothiazole-1,1-dioxide moiety and a 2,3-dihydronaphtho-1,2-thiazine-1,1-dioxide moiety; and Z is a carbonyl moiety containing a

group bonded to the N atom of said ring-closing moiety that undergoes an irreversible cleavage reaction in alkaline solution above a predetermined alkaline pH.

52. A photosensitive element as defined in claim 51 wherein said support carries a red-sensitive silver halide emulsion layer, a green-sensitive silver halide emulsion layer, and a blue-sensitive silver halide emulsion layer, said red-sensitive silver halide emulsion having associated therewith a cyan image dye-providing substance, said green-sensitive silver halide emulsion having associated therewith a magenta image dye-providing substance, and said blue-sensitive silver halide emulsion having associated therewith a yellow image dye-providing substance, each said image dye-providing substance being selected from the group consisting of image dyes and image dye intermediates, the outermost said silver halide emulsion layer carried by said support carrying said substantially colorless optical filter agent precursor activated at an alkaline pH to form a colored optical filter agent.

53. A photosensitive element as defined in claim 52 wherein said image dye-providing substances are, respectively, a cyan dye developer, a magenta dye developer and a yellow dye developer.

* * * * *